(12) United States Patent
Butler et al.

(10) Patent No.: US 9,709,485 B1
(45) Date of Patent: Jul. 18, 2017

(54) DIFFERENTIAL EXCITATION SPECTROSCOPY II

(71) Applicants: Eugene W Butler, Corales, NM (US); Timothy M Stratman, Corrales, NM (US); Boyd V Hunter, Albuquerque, NM (US); Paul Harrison, Rio Rancho, NM (US); Jason M Cox, Albuquerque, NM (US)

(72) Inventors: Eugene W Butler, Corales, NM (US); Timothy M Stratman, Corrales, NM (US); Boyd V Hunter, Albuquerque, NM (US); Paul Harrison, Rio Rancho, NM (US); Jason M Cox, Albuquerque, NM (US)

(73) Assignee: Kestrel Corporation, Albuquerque, NM (US)

( * ) Notice: Subject to any disclaimer, the term of this patent is extended or adjusted under 35 U.S.C. 154(b) by 0 days.

(21) Appl. No.: 15/184,112

(22) Filed: Jun. 16, 2016

Related U.S. Application Data

(63) Continuation of application No. 14/473,796, filed on Aug. 29, 2014, now Pat. No. 9,395,311.

(Continued)

(51) Int. Cl.
   *G01N 21/35* (2014.01)
   *G01N 22/00* (2006.01)
   *G01N 21/31* (2006.01)

(52) U.S. Cl.
   CPC ............. *G01N 21/35* (2013.01); *G01N 22/00* (2013.01); *G01N 2021/3125* (2013.01)

(58) Field of Classification Search
   CPC ........ G01N 21/27; G01N 22/00; G01N 21/35; G01N 2021/3125
   See application file for complete search history.

(56) References Cited

U.S. PATENT DOCUMENTS

| | | |
|---|---|---|
| 2004/0251408 A1 | 12/2004 | Hirano et al. |
| 2006/0049356 A1 | 3/2006 | Shen et al. |

(Continued)

OTHER PUBLICATIONS

A Double Resonance Approach to Submillimeter/Terahertz Remote Sensing to Atmospheric Pressure. Authors: Frank C. De Lucia, Douglas T. Petkie and Henry O. Everitt.

(Continued)

*Primary Examiner* — David Porta
*Assistant Examiner* — Faye Boosalis
(74) *Attorney, Agent, or Firm* — DeWitt M. Morgan

(57) ABSTRACT

A new technique which uses a pump-probe methodology to place a molecule into one or more excited rotational and/or vibrational states. By evaluating spectral changes due to at least one discrete frequency of pump photons a multi-dimensional characterization of the molecule's excited state energy level results. This multi-dimensional characterization typically involves evaluating the changes between excited and unexcited state measurements. The differential nature of the evaluation makes the technique self-referencing and solves problems common to many spectroscopic techniques. The multi-dimensionality of the technique provides high specificity and immunity to interferents. The preferred embodiments involve excitation by using photons suited to pumping the rotational states and evaluating the effects by probing the energy levels of one of more vibrational states. The technique is capable of detecting bulk and trace concentrations of a molecule in gas, liquid and solid phases, both in pure form and in the presence of other molecules.

11 Claims, 23 Drawing Sheets

Related U.S. Application Data

(60) Provisional application No. 61/877,144, filed on Sep. 12, 2013.

(56) References Cited

U.S. PATENT DOCUMENTS

| | | |
|---|---|---|
| 2006/0217911 A1 | 9/2006 | Wang |
| 2008/0024113 A1 | 1/2008 | Mihaila |
| 2009/0237666 A1 | 9/2009 | Vollmer et al. |
| 2013/0123639 A1* | 5/2013 | Ando ............ A61B 5/0059 |
| | | 600/473 |

OTHER PUBLICATIONS

Infrared/Submillimeter Double Resonance as an Approach to Atmospheric Remote Sensing: Measurements and Energy Transfer Modeling. Authors: Jennifer Holt, Ivan R. Medvedev, Christopher F. Neese, Frank C. De Lucia, Dane J. Phillips, Elizabeth A. Tanner, Henry O. Everitt.
Infrared/Terahertz Double Resonance for Chemical Remote Sensing: Signatures and Performance Predictions, Authors: Dane J. Phillips, Elizabeth A. Tanner, Henry O. Everitt, Ivan R. Medvedev, Christopher F. Neese, Jennifer, Holt Frank C. De Lucia.

\* cited by examiner

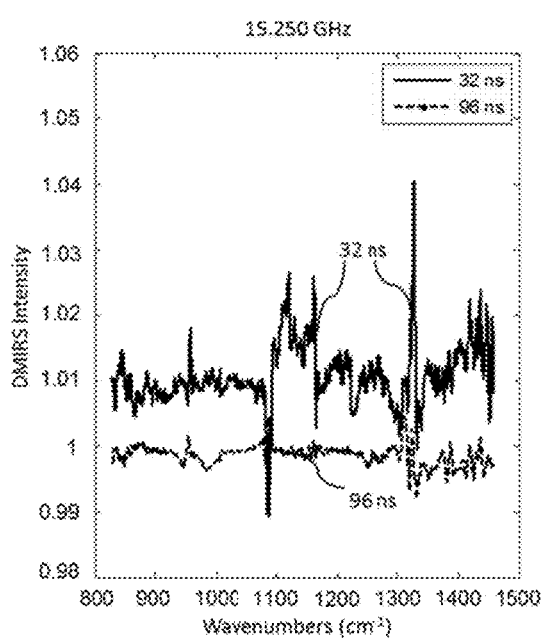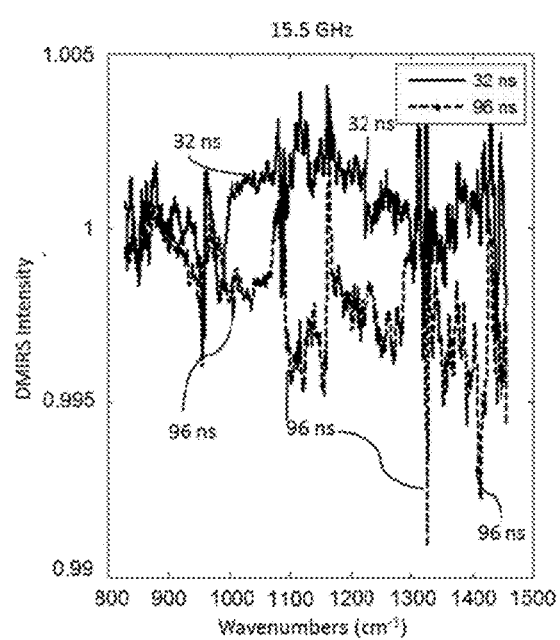
FIG 14E                                   FIG 14F

| PW(ns) | 4.116 | 4.521 | 9.698 | 13.0 | 13.250 | 13.5 | 15.0 |
|---|---|---|---|---|---|---|---|
| 32 ns | Tdg (N.O.) DMMP (N.O.) Mix (N.O.) | Tdg (N.O.) DMMP (N.O.) Mix (N.O.) | Tdg (N.O.) DMMP (N.O.) Mix (N.O.) | Tdg. (+) DMMP (N.O.) Mix (+) | Tdg. (+) DMMP (N.O.) Mix (+/-) | Tdg. (+) DMMP (N.O.) Mix (+) | Tdg. (+/-) DMMP (N.O.) Mix (+/-) |
| 208 ns | Tdg (N.O.) DMMP (-) Mix (-) | Tdg (N.O.) DMMP (N.O.) Mix (N.O.) | Tdg (N.O.) DMMP (+) Mix (+) | Tdg. (N.O.) DMMP (N.O.) Mix (N.O.) | Tdg. (+) DMMP (N.O.) Mix (+) | Tdg. (N.O.) DMMP (N.O.) Mix (N.O.) | Tdg. (+) DMMP (N.O.) Mix (+) |
| 2.56 ns | Tdg (N.O.) DMMP (-) Mix (-) | Tdg (N.O.) DMMP (N.O.) Mix (+/-) | Tdg (N.O.) DMMP (+) Mix (+) | Tdg. (N.O.) DMMP (+) Mix (+) | Tdg. (N.O.) DMMP (N.O.) Mix (N.O.) | Tdg. (N.O.) DMMP (N.O.) Mix (N.O.) | Tdg. (N.O.) DMMP (N.O.) Mix (N.O.) |

FIG 15

FIG 16A
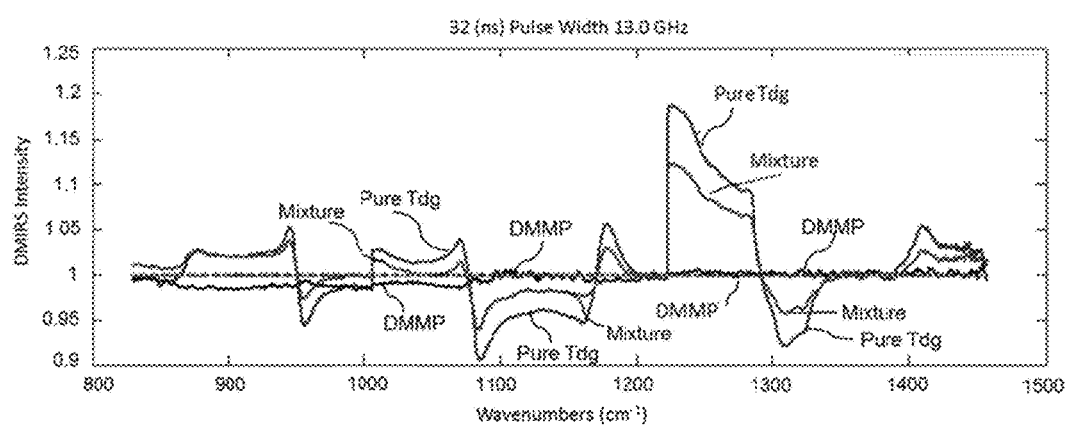
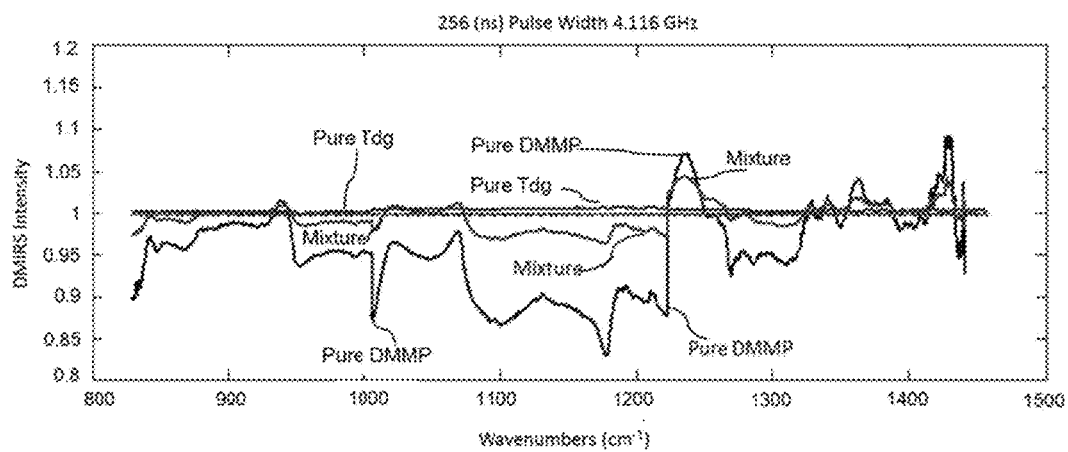
FIG 16B

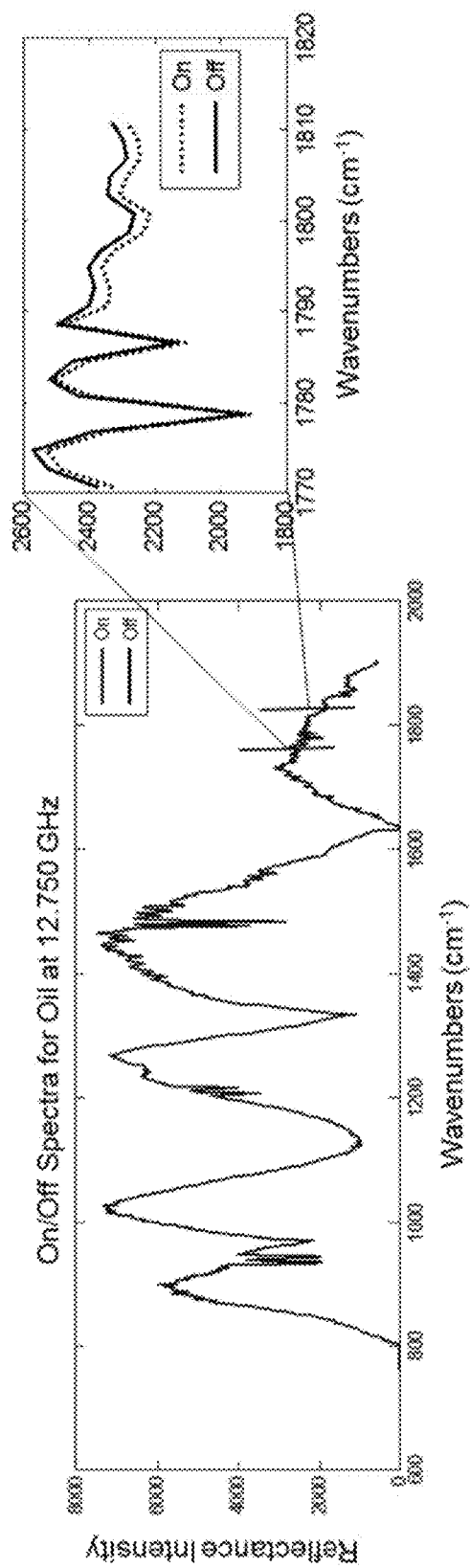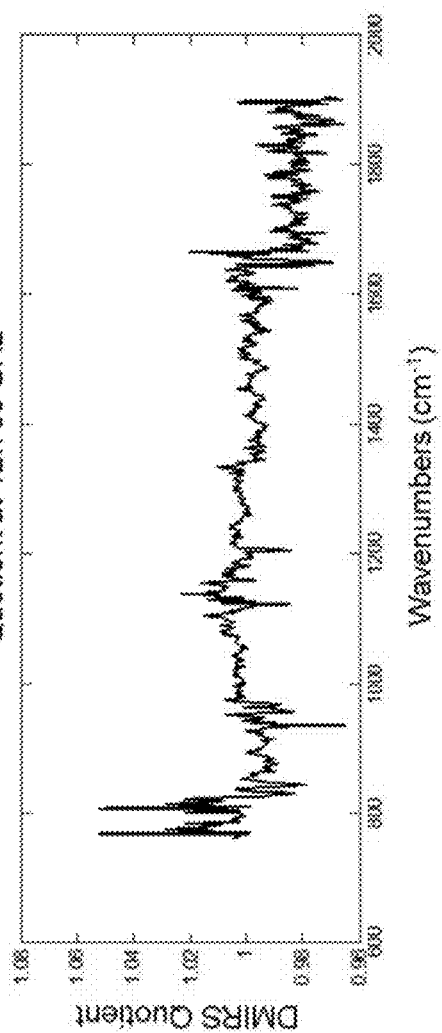
FIG 18A
FIG 18B

DIFFERENTIAL EXCITATION SPECTROSCOPY II

CROSS-REFERENCE TO RELATED APPLICATION

This application is a continuation of application Ser. No. 14/473,796 filed Aug. 29, 2014 which, in turn, is continuation-in-part of provisional application Ser. No. 61/877,144, entitled "Differential Microwave Excitation Infrared Spectroscopy", filed Sep. 12, 2013. This application claims the priority to and the benefit of such applications. The disclosures thereof are incorporated herein by reference.

FIELD OF THE INVENTION

This invention relates to a new spectroscopic technique called Differential Excitation Spectroscopy (DES), which uses a pump-probe methodology to place a molecule into one or more excited rotational and/or vibrational states (hereafter collectively referred to as "rovibrational" states). By evaluating the spectral changes due to the one or more discrete frequencies of pump photons, instead of the one dimensional measure of a molecule (a spectral response curve) that is common to many spectroscopic techniques, a multi-dimensional characterization of the molecule's excited state energy level structure results. This multi-dimensional characterization typically involves evaluation the changes between excited state (or perturbed) and unexcited (or base) state measurements; the differential nature of the evaluation makes the technique self-referencing and solves many problems common to many spectroscopic techniques. The multi-dimensionality of the technique provides high specificity and immunity to interferents. The preferred embodiments involve excitation by using photons suited to pumping the rotational states and evaluating the effects by probing the energy levels of one or more vibrational states. The technique is capable of detecting both bulk and trace concentrations of a molecule in the gas, liquid and solid phases, both in pure form and in the presence of other molecules.

BACKGROUND

Presently, numerous options exist for chemicals and materials detection involving laboratory and field-based monitoring, verification and accounting (MVA) sensors and techniques that can quantify emissions. MVA techniques include atmospheric monitoring technologies, remote sensing and near-surface monitoring technologies, and intelligent monitoring concepts. Specific technological approaches include: atmospheric point samplers ("sniffers" based upon a wide-range of techniques such as electrochemical (membrane), infrared, semiconductor, and ionization/ion mobility); eddy covariance (a.k.a., eddy correlation and eddy flux, including fiber optic sensor arrays based upon photonic bandgap (PBG)); gas chromatography (GC) and accelerator mass spectroscopy (AMS) techniques (including thermal desorption, chemoluminescence, time-of-flight mass spectrometry techniques); acoustic wave and ultrasonic detection; photoacoustic spectroscopy; laser fluorosensor (LFS) (fluorescence energy measurement); various Raman scattering techniques; gamma-ray spectroscopy; laser holographic sensing; various satellite and airborne sensors; and spectroscopic techniques such as back-scatter Light Detection and Ranging (LIDAR), laser-based Differential Absorption LIDAR (DIAL), and Differential Optical Absorption Spectroscopy (DOAS).

However, despite the large number of possible detection technologies, a number of challenges remain to be addressed: (1) the environmental background flux which continues to adversely affect detection sensitivity; (2) turning measurements into an appropriate area-integrated, mass balance (quantity) is difficult; (3) small "patch" area samples which are not ideally suited for cost-effectively and comprehensively observing a large area; and (4) the statistical "spatial resolution" of present monitoring systems is too coarse and, thus they are unable to easily (e.g., rapidly) locate and characterize an individual hazard (e.g., threat) within the larger landscape (e.g., separate one contaminated vehicle out of many uncontaminated vehicles).

With specific regard to detection sensitivity and operating in the real world, many anthropogenic emissions are present that negatively affect relevant measurements systems. For example: normal vehicle emissions such as ammonia ($NH_3$); carbon black from tires and combusted diesel; production of electricity; cement, chemical/fertilizer, mining and ethanol emissions; pollen and attractants from certain flowering plants; volatile organic compounds (VOCs); farming and ranching practices such as pesticide and herbicide application; and fine particulate matter in the air. Furthermore, natural skin oils (e.g., squalene), chemicals used in processed food (e.g., binders and preservatives), certain soaps/shampoos, deodorants/antiperspirants, perfumes/colognes, and insect repellents are all known to confuse or unfavorably affect the sensitivity of many detection techniques. In these environments and situations not only is the detection of a specific gaseous, vapor/aerosol, solid or liquid species complicated by the background and contaminates present, but these naturally occurring and anthropogenic sources of interferents will spoof many present detection techniques with false readings concerning an actual hazard.

Thus, there are few analytic tools available that can be used to quantify and characterize, non-intrusively (not slowing or down-grading the testing tempo, along with supporting moving object testing modalities) and in situ at the low concentrations typically required (in the low parts-per-billion to low parts-per-trillion range). While many techniques from material sciences are pertinent, each one has shortcomings that prevent its widespread adoption in a real-time production setting. More importantly, many measurement techniques, which might be considered for use, are unable to adequately distinguish chemicals of interest from interferents; such interferents often being the result of human-caused situations, or naturally occurring sources. Furthermore, there may be practical confusion of the significance of a detection event due to many chemicals' dual-use applications. Even under well controlled conditions, background sources may dominate over the target materials of interest. Viable solutions are further complicated when the desire is a single detection technology that needs to detect a wide-range of chemicals with significantly different molecular structures, in multiple phases (solid, liquid and/or gas) of matter, instead of just a few closely related species in a single phase of matter. Therefore, a way to easily and affordably distinguish different sources would be of practical value to chemical and materials detection. In contrast to the prior art, the DES technique of the present invention offers agility in the range of detectable species, in all phases (solid, liquid and gas) of matter, and has a unique tolerance to interferents.

SUMMARY OF THE INVENTION

The invention relates to a method of detecting the presence of a molecular species in a sample utilizing one or more frequencies of electromagnetic radiation, including frequencies matched to the molecular species' rovibrational energy levels, for perturbing the rovibrational density of states of the molecular species (hereinafter the "matched frequencies"). The method, which utilizes means for assessing the spectral response of the molecular species in its perturbed and unperturbed states and for assessing the presence of the molecular species in the sample, includes: assessing the rovibrational density of states of the molecular species as manifested by its spectral response in at least one region of the electromagnetic spectrum; assessing the perturbed state of the molecular species by perturbing the rovibrational density of states of the molecular species using frequencies of electromagnetic radiation selected from the matched frequencies and determining the effects of the perturbation on the spectral response of the rovibrational density of states of the molecular species; and assessing the effect the perturbation had on the molecular species using its perturbed and unperturbed spectral responses. Assessing the rovibrational density of states of the molecular species (as manifested by its spectral response in the at least one region of the electromagnetic spectrum) includes interrogating the molecular species with electromagnetic radiation in the at least one region of the electromagnetic spectrum to determine an unperturbed spectral response of the rovibrational density of states of the molecular species. Assessing the spectral response of the perturbed rovibrational density of states of the molecular species includes illuminating the molecular species with electromagnetic radiation frequencies selected from the matched frequencies and interrogating the molecular species with electromagnetic radiation in the at least one region of the electromagnetic spectrum to determine a perturbed spectral response of the rovibrational density of states of the molecular species. The means includes means for determining the change between the spectral response of an unperturbed and a perturbed rovibrational density of states of the molecular species and further including determining the change between the spectral response of the unperturbed and the perturbed rovibrational density of states of the molecular species. Though stated in a particular order, no representation is made or intended that this order is always necessary.

The method further utilizes means for determining the concentration of the molecular species in the sample, and determining the concentration of the molecular species in the sample (which may contain one or more molecular species). More specifically, this uses: the relative difference between the spectral response of the unperturbed and the perturbed rovibrational density of states of a molecular species in a sample to determine the concentration of the molecular species in the sample; the relative response of the molecular species within the sample at a known power of frequencies of electromagnetic radiation selected from the matched frequencies for perturbing the rovibrational density of states of the molecular species in the sample; and known conditions for assessing the spectral response of the molecular species in its perturbed and unperturbed states and relating the molecular species' response to a library of calibrated responses collected under the same conditions from known concentrations of the molecular species. The method includes: assessing the rovibrational density of states of the molecular species as manifested by its spectral response in at least one region of the electromagnetic spectrum under known assessment conditions; assessing the perturbed state of the molecular species by perturbing the rovibrational density of states of the molecular species using by using known powers of frequencies of electromagnetic radiation selected from the matched frequencies and determining the effects of the known perturbation on the spectral response of the rovibrational density of states of the molecular species; and assessing the effect the perturbation had on the molecular species using its perturbed and unperturbed spectral responses as related to a pre-compiled library of calibrated responses from known concentrations of the molecular species.

The method also includes detecting the presence of at least one additional molecular species in a sample ("additional molecular species") utilizing one or more frequencies of electromagnetic radiation, including frequencies matched to the additional molecular species' rovibrational energy levels, for perturbing the rovibrational density of states of the additional molecular species ("additional matched frequencies"). This includes: assessing the rovibrational density of states of the additional molecular species as manifested by its spectral response in at least one region of the electromagnetic spectrum; assessing the perturbed state of the additional molecular species by perturbing the rovibrational density of states of the additional molecular species using frequencies of electromagnetic radiation selected from the additional matched frequencies and determining the effects of the perturbation on the spectral response of the rovibrational density of states of the additional molecular species; and assessing the effect the perturbation had on the additional molecular species using its perturbed and unperturbed spectral responses.

BRIEF DESCRIPTION OF THE DRAWINGS

FIG. 3A shows the effect on the raw IR spectrum of DMMP; while

FIGS. 14A-F show thiodiglycol modulation as function of pulse width. 32 ns pulses (solid line) and 96 ns pulses (dashed line) are compared at microwave frequencies 13.0 GHz to 15.5 GHz.

FIG. 15 is a table showing an experimental matrix and results for DMMP/Thiodiglycol mixture determination wherein (+)=peak enhancement, (−)=peak suppression, and (N.O.) represents no observable change.

FIGS. 16A and B demonstrate the separability of the thiodiglycol and DMMP responses by using pulse widths and microwave frequencies optimized for particular transitions. The top panel compares pure thiodiglycol to DMMP and a 50/50 thiodiglycol/DMMP mixture with 32 ns laser pulses at 13.0 GHz microwave excitation frequency which parameters excite the thiodiglycol response while generating virtually no response from DMMP. The bottom panel is the same comparison for a 256 ns pulse width at 4.116 GHz which parameters excite the DMMP response while generating virtually no response from thiodiglycol. In both cases the mixture response closely matches the response of the pure component being tested for, while the other species shows minimal response.

FIGS. 18A and B show the DMIRS response (raw data in A, quotient in B) for 5W-30 motor oil using the UN excitation parameters. As indicated in the legend, the dotted line represents "on" spectra; the solid line, "off" spectra.

OVERVIEW OF THE TECHNIQUE

Figure 1:
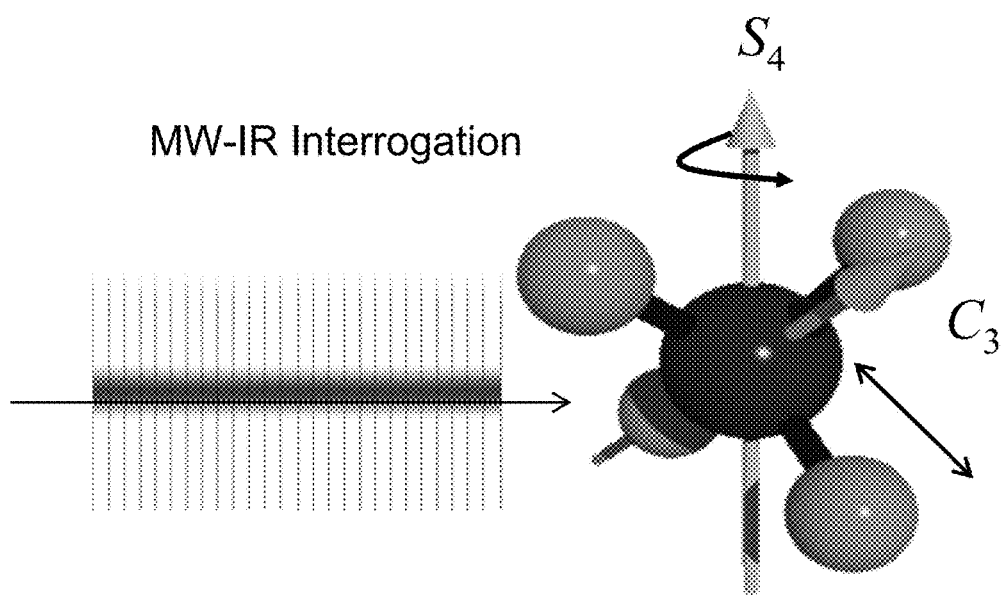
FIG. 1 illustrates the MW-IR double resonance interrogation of a target molecule with microwave energy.

Polyatomic molecules consist of atoms joined together by various strength bonds based on the electronic configuration of their respective electron clouds. The atoms or molecular sub-groups in a material are free to vibrate or oscillate with respect to one another, as would be expected of a bound mechanical system. With reference to FIG. 1, wherein the spheres represent different types of atoms and C3 and S4 refer to possible rotation and vibration axes. (The MW-IR interrogation, discussed below, is also schematically illustrated.) At the simplest level, the molecule can be thought of as a collection of atoms bound together with springs. The molecules also have rotational degrees of freedom (these rotational modes are strongly influenced by the state of matter, being least constrained in gas form and most constrained in solid form). These rotational and vibrational modes are collectively referred to as "rovibrational" modes. The molecular bonds in polyatomic molecules have distinct spectral signatures based on the energy of the bond (analogous to spring stiffness in a conceptual model) as well as the rovibrational mode (type of motion and frequency).

Under the Differential Excitation Spectroscopy (hereinafter "DES") umbrella there are a number of technique variants based on methods of probing the rovibrational states. Two such variants will be referred to herein as Differential Microwave Excitation IR Spectroscopy (hereinafter "DMIRS") and Differential Excitation Raman Spectroscopy (hereinafter "DERS"). The skilled practitioner will recognize that these two specific variants represent a subset of the possible applications of the DES technique. DMIRS is a very practical application in that it uses RF energy to excite the rotational modes (typically from about 100 MHz through 20 THz, depending upon the state of matter, size, shape and symmetry of the molecule) and IR spectroscopy to probe the vibrational response. In a preferred embodiment, the RF energy is in the microwave region (100 MHz to 300 GHz) in order to take advantage of atmospheric transmission windows for applications with significant standoff requirements. DMIRS is only applicable to molecules that are IR-active (i.e. possess at least an instantaneous dipole moment) since IR spectral data is required; some molecules or modes are not IR active. For such molecules, a common measurement approach is Raman spectroscopy, which is based on photon scattering from the molecule. Hence, the extension of DES to IR-inactive materials is to excite the rotational modes as described previously and probe the vibrational modes with the Raman technique—the above named DERS technique. For the purpose of illustrating the physics and applications of the DES technique, specific examples using the DMIRS technique are discussed below as illustrative, but not limiting, examples. Thus, the invention is not limited to the use of either IR or microwave radiation.

Background Physics of DMIRS

The DMIRS effect is a novel technique that enables molecular rovibrational states to be directly probed using relatively simple pieces of equipment. It is a novel adaptation of pump-probe spectroscopic techniques being applied to the molecular rovibrational states. Because of the low energies of the rotational modes, microwave photons are used as the pump source between rotational modes (J states) and higher-energy IR photons are used as the probe mechanism, as they match the energy differences between the vibrational energy levels (v states) as depicted in FIGS. 2A and B.

Figure 2A:
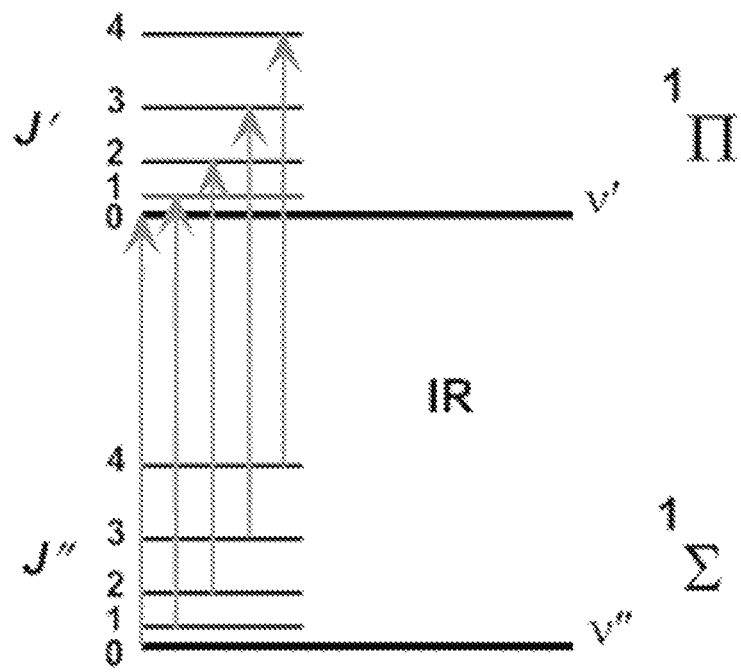
FIGS. 2A and B are rovibrational transition diagrams between two vibrational singlet states for conventional infrared absorption (FIG. 2A) and for the microwave-infrared double resonance technique of the present invention (FIG. 2B).
Figure 2B:
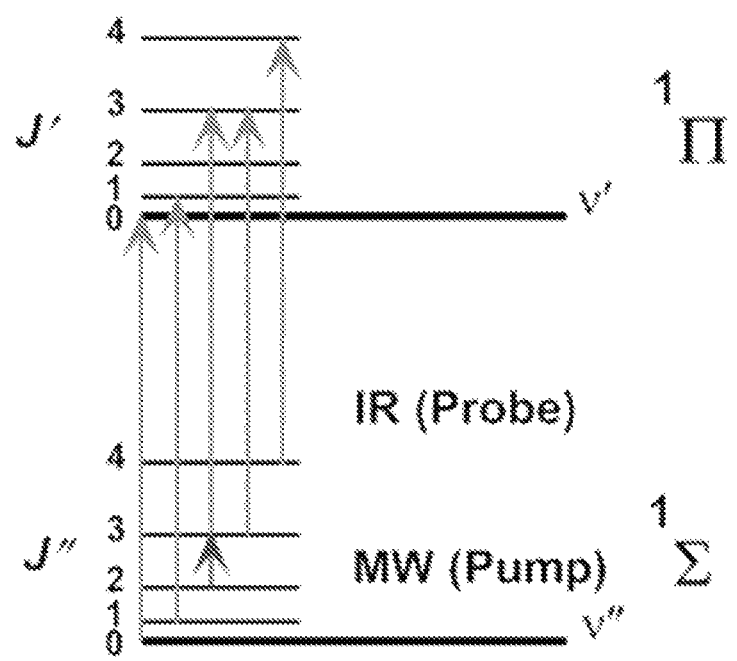

The transition mechanism depicted in FIG. 2A represents conventional IR absorption involving one vibrational level transition (v"→v') over a manifold of rotational states (illustrated as J"≤4 and J'≤4) under arbitrary thermal equilibrium of the molecule. FIG. 2B represents the DMIRS effect, in which one or more of the lower-state rotational levels is purposely excited (perturbed) at a MW frequency in resonance with its quantum-mechanically allowed rotational transition (i.e., pump), while a second photon source (i.e., probe) causes a resonance transition involving one vibrational level; hence, a double resonance effect. With a significant population of rotationally-perturbed states affected by the resonance conditions for MW excitation (FIG. 2B), the net effect on observing (or probing) the infrared absorption (or reflectance) spectrum is a change in the shape and intensity of spectral bands corresponding to the IR resonance of the vibrational transition due to an enhancement or attenuation of rovibrational transition probabilities and state-to-state lifetimes as compared with pure IR spectroscopy (FIG. 2A). This is most clearly illustrated when comparing the $J''=2$ and $J''=3$ states in FIG. 2A and FIG. 2B, it is clear that the DMIRS effect has reduced the population of the $J''=2$ to $J'=2$ state and increased the population of the $J''=3$ to $J'=3$ state, i.e. spectral suppressions and enhancements are observed in the raw data.

Figure 3A:
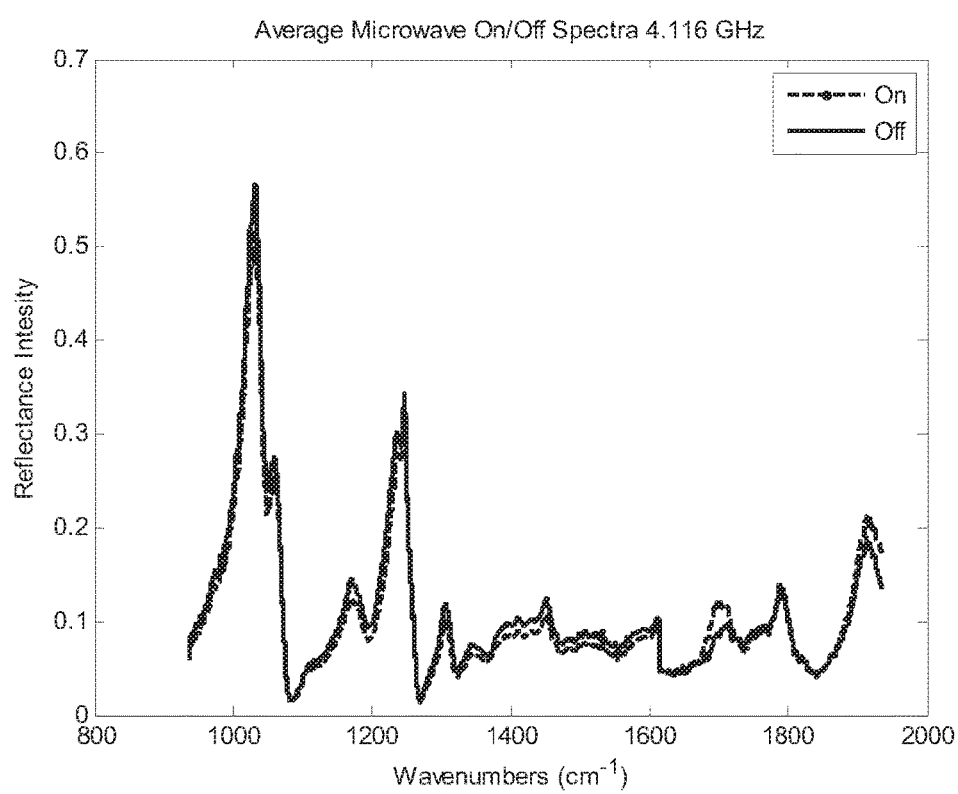
FIGS. 3A and B illustrate the "DMIRS" (defined below) effect.
Figure 3B:
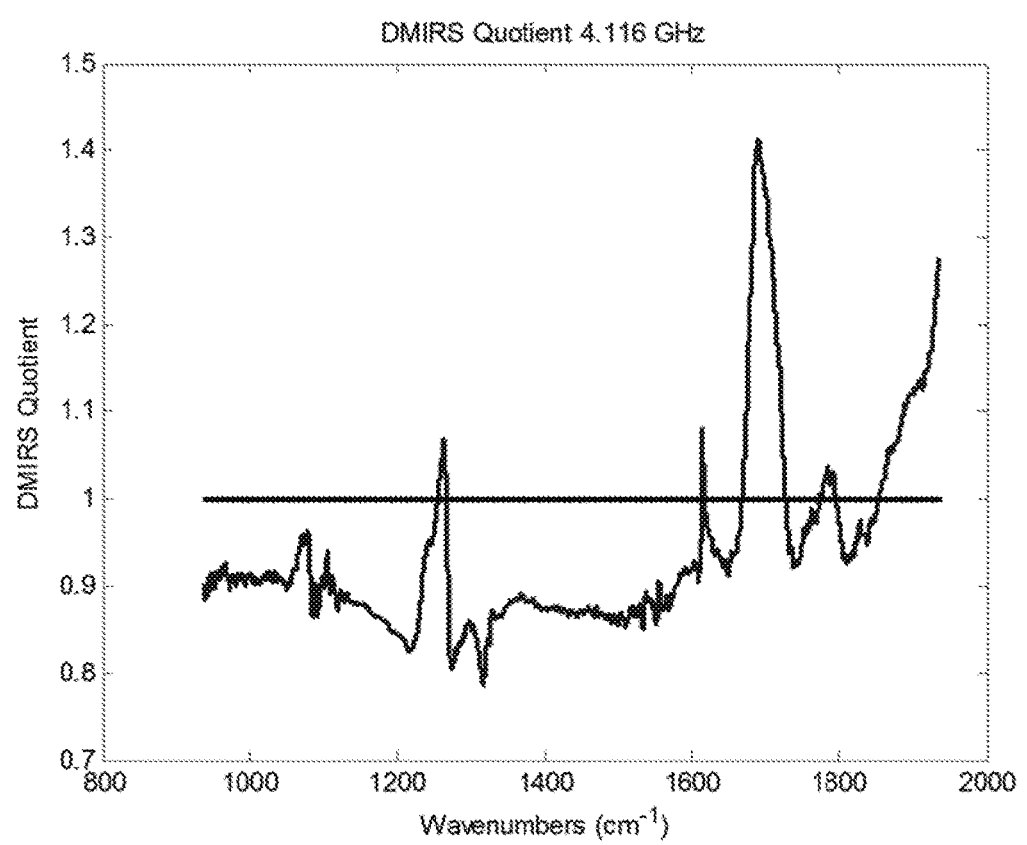
FIG. 3B shows the "processed" spectrum (the quotient of the RF on/RF off spectra). This is a preferred means for visualizing the effect.

Because the technique compares the changes between the unexcited and excited IR spectra, the vagaries of the underlying IR spectrum (which is a convolution of the incident IR energy and spectral responses of the substrate and surface contaminants) are unimportant, as the process of comparing the differences results in a self-referencing technique. This avoids a common problem with IR spectroscopy. An example of the effect is shown in FIGS. 3A and B, where the gross spectral modifications due to the DMIRS effect are seen in FIG. 3A (this is the physical manifestation of the effect), and the DMIRS quotient ("RF on" signal normalized by the "RF off" signal) is shown in FIG. 3B. The DMIRS quotient is an easy mechanism for visualizing the enhancement and suppressions caused by the effect as well as the locations of the effect without the complications of underlying raw spectral features. This is how the self-referencing is accomplished.

In conventional IR spectroscopy, the result is an absorption or transmission graph—a 1D representation of the convolution of the density of states at a specific temperature (the distribution is a function of temperature) and the transition probabilities for each of the possible states. It is clear from the discussion of the previous paragraph that DES uses the probe wavelength ($\lambda$) and adds another dimension to the characterization of the excited states: the frequency of the pump or excitation photons ($\nu$), which perturb the rovibrational density of states. Our research has demonstrated yet another strong dimension to the process: the duration of the probe pulse ($\tau$). These multiple dimensions for characterization of the material provide built-in robustness to the technique, thus improving the specificity and reliability of the results and are important detection parameters.

The detection parameters may be determined in two ways. First, a brute-force search of the ($\lambda,\nu,\tau$) parameter space may be conducted. This can be very difficult because the optimal conditions may show high finesse, i.e. the allowable error around the optimal value may be very small, necessitating a very fine grid and hence a great deal of time for the search. Second, the molecule of interest is modeled, typically as an ab initio calculation to determine the shape of the potential energy surface and hence the energy levels and required wavelength and frequency parameters. This is the preferred approach because it directs the work efficiently. However, this work is not trivial and the structure of some molecules may exceed the capabilities of available modeling tools.

Early work performed with the above technique used CW illumination and FTIR spectrometers as the detection technique. Recent availability of Quantum Cascade Lasers has made it possible to examine a materials response to pulsed probe illumination. The variable pulse width of the QCL allows the lifetimes to be evaluated, as the DMIRS effect is significantly enhanced when the IR probe beam pulse duration is comparable to (in resonance with) the state lifetime of the vibrational mode being probed.

Description of the Preferred Embodiments and Test Data

With this invention, we have developed a novel molecular conditioning technique which allows the density of states of a molecule to be perturbed from a normal ground state distribution through the application of a pump radiation field. The pump radiation field, subject to the normal constraints of transition probability and absorption cross-section, preferentially alters the molecular rotational and vibrational states (again, the rovibrational states) in favor of higher-order modes. This perturbation of the density of states is physically manifested by alterations to the spectrum for the material, with certain portions of the spectrum being strengthened (enhanced) or weakened (suppressed), depending on the applied perturbation. These changes in the spectrum are a sensitive indicator of the underlying molecular species rovibrational states, as a correctly applied perturbation will force the molecule into another state. This distribution of states is highly specific to a molecular species, and similar, but not identical molecular species would not be expected to have the same distribution of states. Hence this technique is a sensitive probe into the detailed density of states for a specific molecular species and is an orthogonal measurement to conventional spectroscopy, as the technique probes more parameters than the ground state distribution. Its implicit reliance on a unique density of states makes it dramatically less susceptible to confusion by similar molecular species (e.g., interferents). It is possible to reach more highly excited states by either using higher energy photons or by applying multiple lower energy photons to reach these states. For a variety of practical reasons, such as the atmospheric attenuation, in DMIRS applications microwave energy is the preferred form of pump radiation.

A microwave region of interest for a preferred embodiment of the technique is between 100 MHz through 300 GHz and encompasses the frequency band containing the fundamental rotational resonance frequencies of many molecules composed of carbon, nitrogen, oxygen and sulfur. As an inherently differential technique, this novel approach is intrinsically self-referencing, providing a spectroscopic signature that shows high immunity to spectral interference from background and radiation source variations. In a preferred implementation, the DMIRS response is calculated as the quotient of the "microwave on" and "microwave off" spectra, i.e. the spectra collected with and without the pump (or perturbation) radiation source being active. There are a series of probe wavelengths, pump frequencies, and probe pulse duration parameters that provide a multi-dimensional characterization of a molecule's excited state energy structure. The essential value of this higher-dimensionality signature is that the probability of true detection is higher and background interference less important.

In practice, as mentioned above, the proper combination of spectral regions (e.g., microwave-IR spectral regions) can be determined empirically by scanning various combinations of electromagnetic radiation (e.g., the optical and microwave radiation) to determine the responses and the unique signature. Alternatively, as also mentioned above, computational modeling of the molecule to determine its structure and potential energy surface function can be used to determine appropriate combinations of electromagnetic radiation frequencies.

Figure 4:
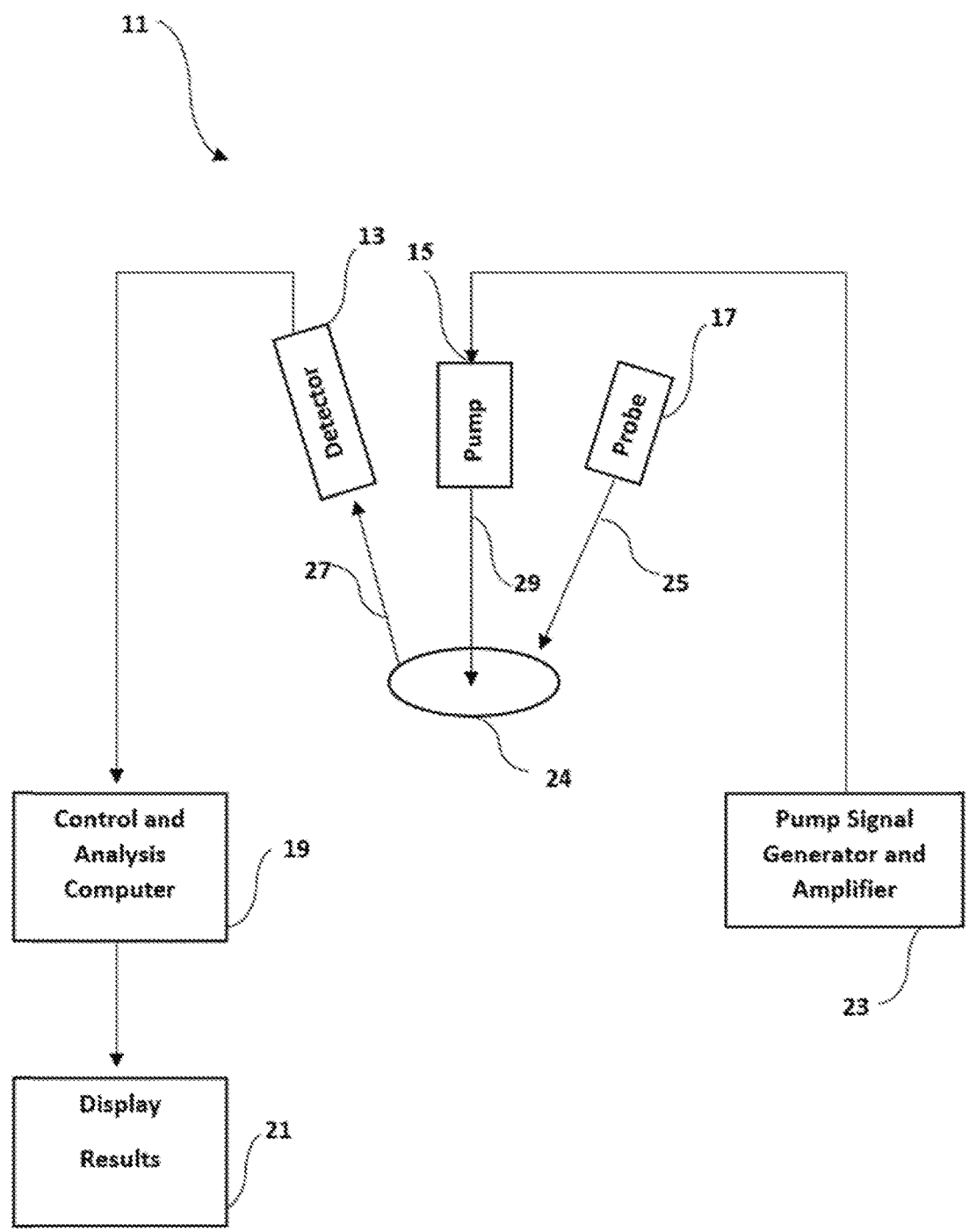
FIG. 4 illustrates a schematic of the apparatus of the present invention in association with the DMIRS testing of solids and liquids.

The basic DMIRS apparatus 11 for use in association with testing solids and liquids, as is set forth in FIG. 4, includes detector 13, pump 15, and probe 17. As illustrated, detector 13 is connected to control and analysis computer 19, which includes a screen 21 for displaying the results of test on a sample including at least one molecular species. As is also illustrated, pump 15 is coupled to pump signal generator and amplifier 23. One of the benefits of the present novel method is that it may use off the shelf components. Thus, by way of example (but not limitation): detector 13 is a MCT detector capable of detecting MWIR and LWIR radiation; pump 15 is an RF emitter (e.g., antenna or horn); probe 17 is a quantum cascade laser; control and analysis computer 19 is a commercial personal computer; display/screen 21 provides a mechanism for control inputs from the user, and display of results (this is generally considered part of the computer); and pump signal generator and amplifier 23 is a commercial RF frequency generator with amplifiers to increase the emitted pump radiation power. Control and analysis computer includes one or more data bases, including one in which a library of responses to the DES technique is stored.

In a mode of operation the rovibrational density of states of a sample 24 (e.g., a molecular species) is assessed by exposing it to electromagnetic radiation 25 from probe 17 to determine an unperturbed response of the molecular species. The response signal 27 is detected by detector 13 and transmitted to control and analysis computer 19. Perturbing the rovibrational density of states of sample 24 by illuminating it with one or more frequencies of electromagnetic radiation 29, including frequencies matched to the molecular species rovibrational energy levels, is affected by pump signal generator and amplifier 23 and pump 15. The perturbed state of the molecular species is assessed (interrogated) by probe 17 and detector 13 and transmitted to control and analysis computer 19 where the effect the perturbation had on the molecular species (using its perturbed and unperturbed spectral response) is assessed. Control and analysis computer includes a routine for determining the change between the spectral response of the unperturbed and the perturbed rovibrational density of states of the molecular species. The results may be displayed on display/screen 21.

The difference between the spectral response of the unperturbed and the perturbed rovibrational density of states of a molecular species in a sample may be used, by a routine(s) in control and analysis computer 19 to determine the concentration of the molecular species in the sample. The methodology uses the response of the molecular species within a sample at a known power of frequencies of electromagnetic radiation selected from the matched frequencies for perturbing the rovibrational density of states of the molecular species in the sample and known conditions for assessing the spectral response of the molecular species in its perturbed and unperturbed states and relating the molecular species' response to a pre-compiled library of calibrated responses collected under the same conditions from known concentrations of the molecular species. The library, not shown, is stored in control and analysis computer 19. The method includes: assessing the rovibrational density of states of the molecular species as manifested by its spectral response in at least one region of the electromagnetic spectrum under known assessment conditions; assessing the perturbed state of the molecular species by perturbing the rovibrational density of states of the molecular species using known powers of frequencies of electromagnetic radiation selected from the matched frequencies and determining the effects of the known perturbation on the spectral response of the rovibrational density of states of the molecular species; and assessing the effect the perturbation had on the molecular species using its perturbed and unperturbed spectral responses as related to the pre-compiled library.

While the foregoing is in reference to a sample of a single molecular species, apparatus 11 (as well as apparatus 31, apparatus including cell 43 and apparatus including cell 53, all discussed below) and the methodology of the present invention can be used to detect the presence of one or more additional molecular species included in a sample.

Figure 5:
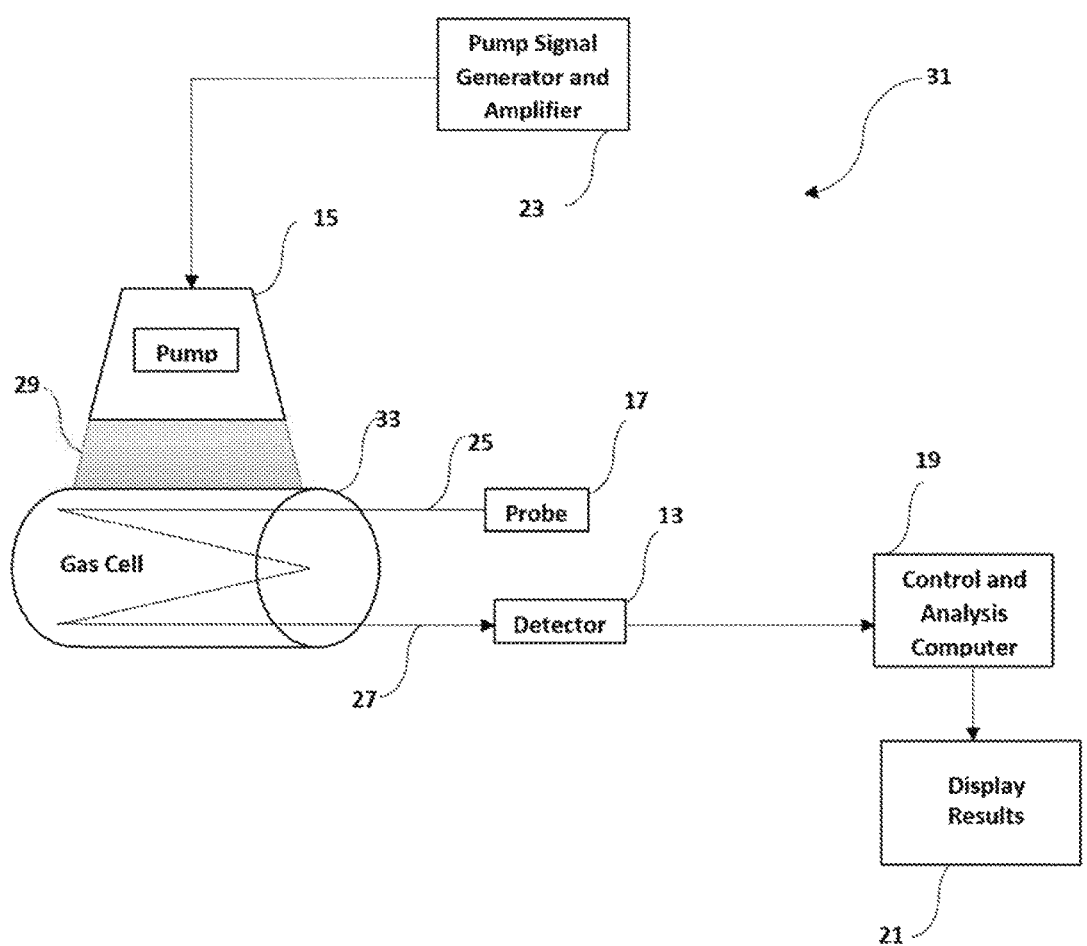
FIG. 5 illustrates a schematic of the apparatus of the present invention in association with the DMIRS testing of gas phase samples.

For the testing of gas phase samples the apparatus 31, as schematically illustrated in FIG. 5, can be used. In addition to detector 13, pump 15, probe 17, control and analysis computer 19, display/screen 21, and pump signal generator and amplifier 23, apparatus 31 includes a gas cell 33, preferably a multi-pass design (e.g., a Pfund, White or Heriott cell geometry (or a functional equivalent)) to increase the effective path length while maintaining compactness. The operation is the same as described above with regard to the apparatus of FIG. 4. Matched frequency radiation 29 takes the form of a wide beam to ensure that the entire volume of gas cell 33 is available to be probed.

Figure 6A:
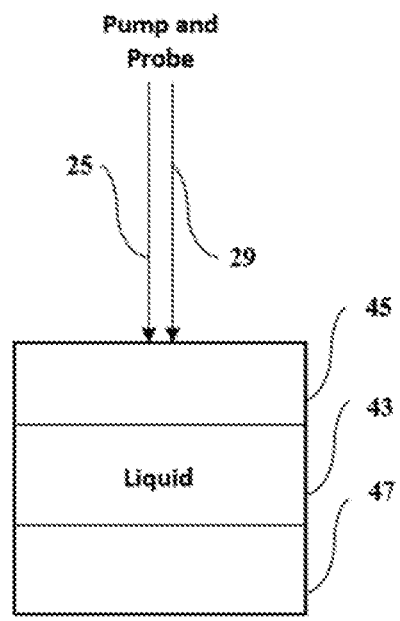
FIGS. 6A and B show two versions of the liquid cell that would be used with, respectively, the apparatus of FIG. 4 (FIG. 6A) and the apparatus of FIG. 5 (FIG. 6B) instead of the gas cell.
Figure 6B:
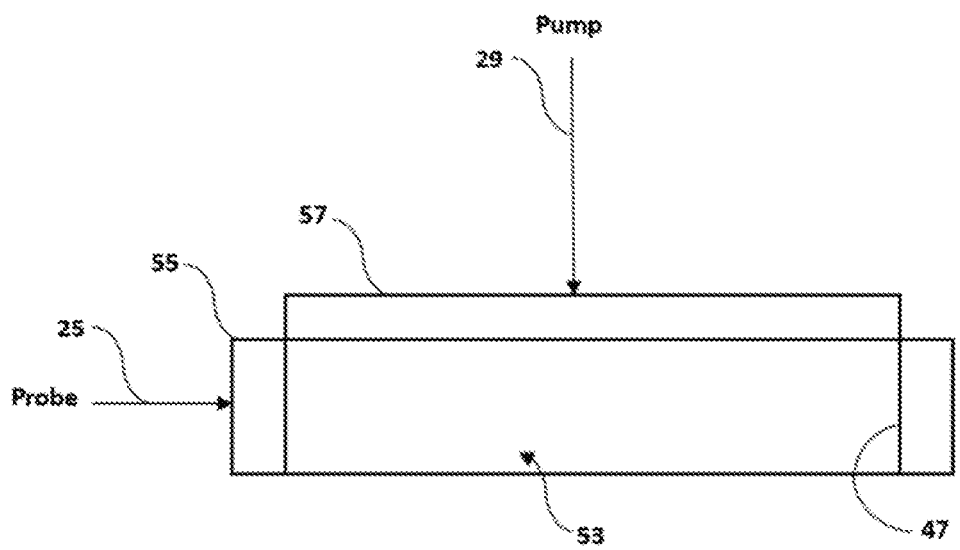

For the testing of bulk liquid samples, the sample 24 of FIG. 4 or the gas cell 33 of FIG. 5 may be replaced by a specially designed liquid cell, optimized to ensure that the volume of the cell is available to be probed by not exceeding the penetration depths of the pump or probe radiation. With the cell in FIG. 6A replacing the sample 24 of FIG. 4, cell 43 has a window 45 that is transparent to both pump and probe radiation and has a reflective substrate (e.g., gold) 47, and may be of either a single reflection or multiple reflection design. Alternatively, as the transmission windows for pump and probe radiation may be incompatible with available window materials, FIG. 6B (which replaces the gas cell 33 of FIG. 5) separates the pump window 55 and probe window 57 of cell 53, so that the pump and probe radiation will be transmitted through different windows. As before, the reflective substrate 47 in conjunction with probe window 57 may be configured in either a single or multiple reflection design. Multiple reflection designs have the advantage of the gas cell 33, in that they increase the mass of material probed, thus increasing ultimate device sensitivity.

The equipment set forth above is intended to be representative, not limiting. Also, such equipment could be used in other DES applications.

Test Results

Different molecules and even different bonds and states of a molecule will, in principle, have different sets of optimal excitation parameters. This is shown in the following sections for four different molecules: DMMP (dimethyl-methylphosphonate), thiodiglycol, RDX (an explosive) and urea nitrate. The TNT test data set forth in provisional application Ser. No. 61/877,144, incorporated by reference, was taken with a CW source and, therefore had lower modulation (no pulse duration modulation).

Liquid: DMMP

Figure 7:
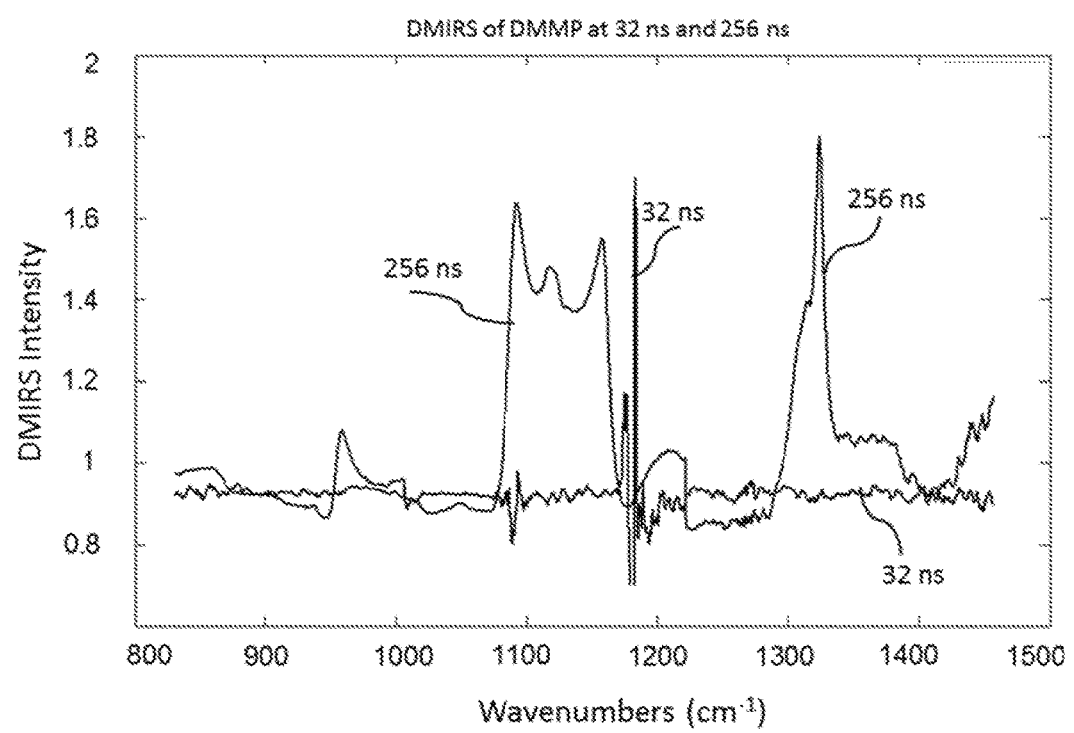
FIG. 7 shows the effect of pulse width on DMMP (dimethyl-methylphosphonate) for microwave excitation at 9.698 GHz.

FIG. 7 shows the DMIRS quotient for DMMP under the same excitation conditions (9.698 GHz microwave frequency). This figure shows the laser transition points at 1006 and 1220 cm$^{-1}$ (the discontinuities at these points should be ignored as this is where the probe laser was changed). The figure demonstrates: (1) the very high modulation enhancements that are possible when the pulse width is correctly selected; and (2) different bonds with the same microwave excitation frequency can have very different lifetimes. This latter effect is evident when noting the single, very narrow and strong enhancement at ~1175 cm$^{-1}$ seen at 32 ns versus the wide variety of enhancements seen at 256 ns. Comparing the two plots, one can also see some of the same features (peak locations) in both sets of data, although there may be reversal between enhancement and suppression. There is clearly an enormous amount of complexity and information available in the DMIRS response; this information provides enormous insight into the energy states and transition lifetimes of a molecule of interest. Because DMMP is a more complex molecule, the full material response is also more complex.

Liquid: Thiodiqlycol

Figure 8:
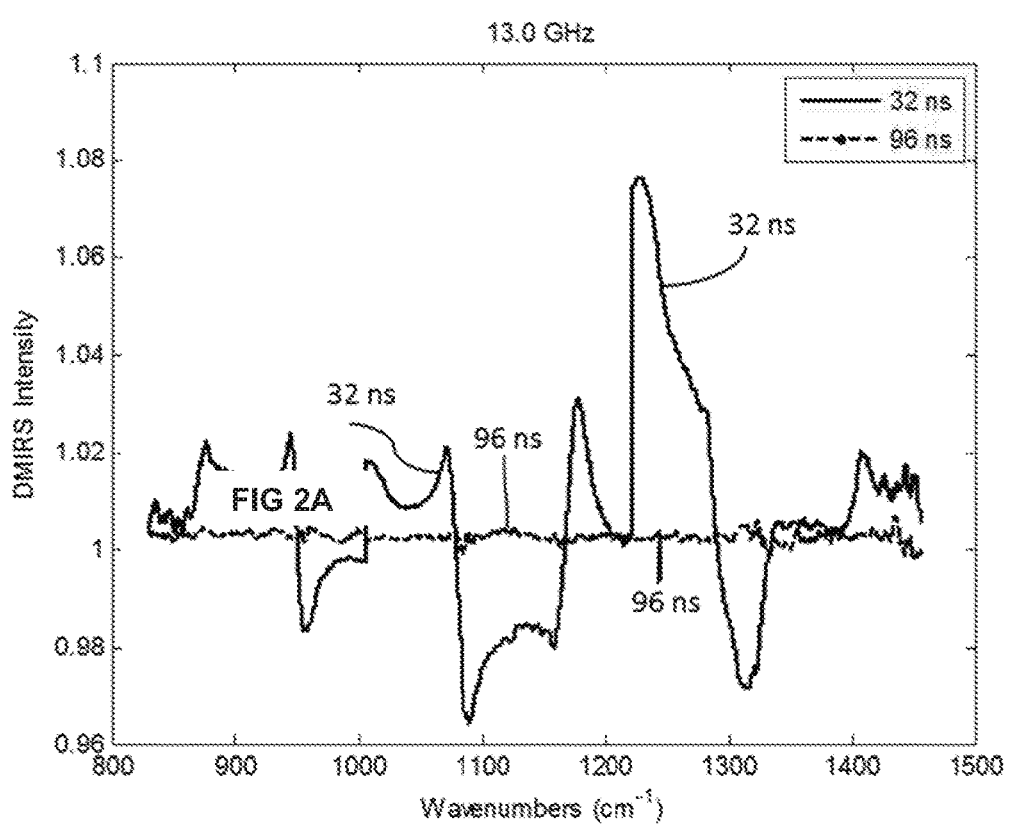
FIG. 8 shows the effect of pulse width on thiodiglycol with 13.000 GHz microwave pump photons.
Figure 9:
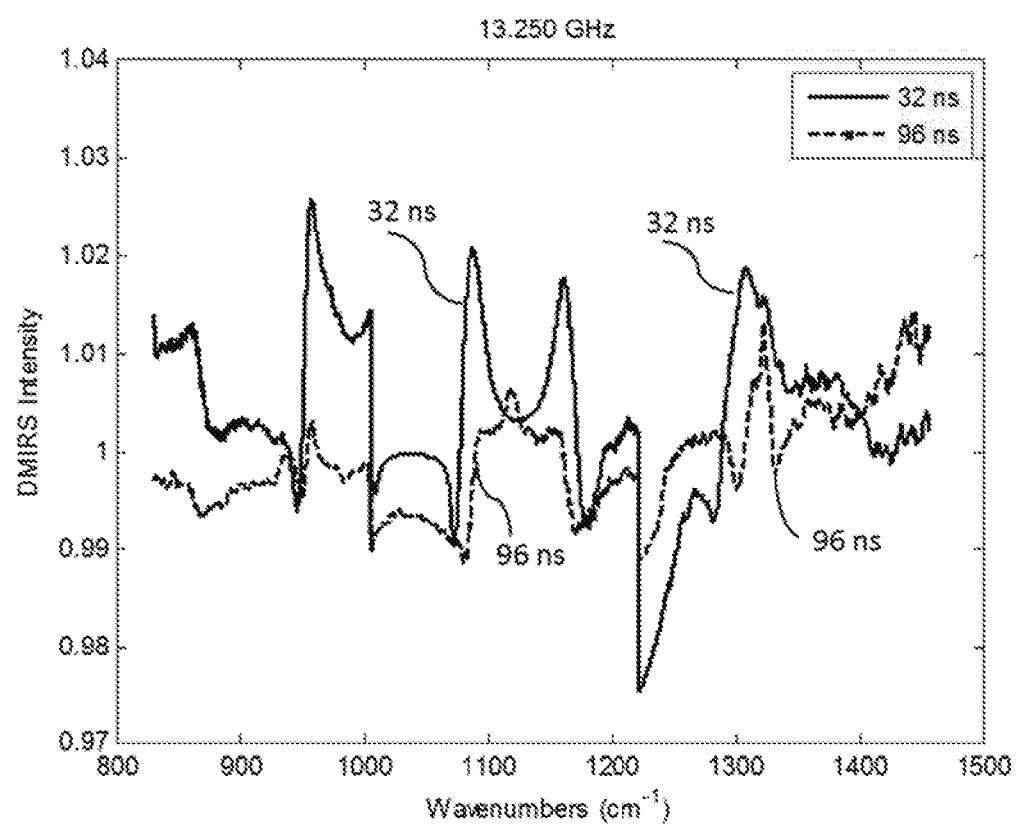
FIG. 9 shows the effect of pulse width on thiodiglycol with 13.250 GHz microwave pump photons.

Thiodiglycol, also a liquid, exhibits the same qualitative pulse width enhancements as DMMP though the specific details are different. FIG. 8 shows the enhancement at 13 GHz for 32 (solid graph) and 96 (dashed graph) ns pulses, with the latter signal being distinguishable from noise only with a priori knowledge of the feature locations (such as the information seen in the enhanced 32 nm spectrum). The suppression blip at approximately 1080 $cm^{-1}$ in the 96 ns pulse curve is an example of the weaker response. FIG. 9 gives a glimpse into the richness of structure that a complex molecule can demonstrate: at 13.250 GHz, the structure of excited states has changed (e.g. consider the features in the 1075-1090 $cm^{-1}$ range: both pulse widths create enhancements, although they are different and may shift). In the ~1325 $cm^{-1}$ range pulse widths drive different shape enhancements (meaning that adjacent features show different resonances) and the suppression seen at 13 GHz (FIG. 8) has now become varying enhancements.

Solid: RDX

Figure 10:
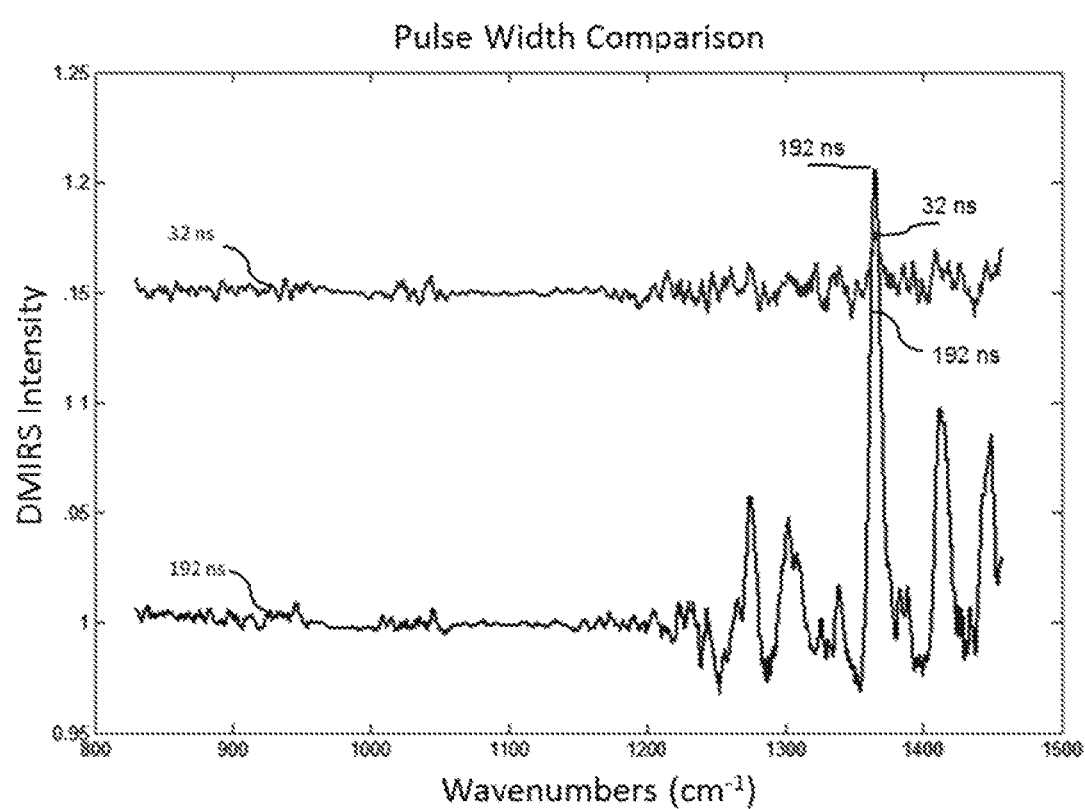
FIG. 10 shows the response of the explosive RDX to 3 GHz pump radiation with 32 and 192 ns pulses. The heightened response at 32 ns is due to matching the resonance condition of the excited state (specific bond, specific vibrational states).

The pulse width dependence of the DMIRS effect is not confined to liquid samples; it is a fundamental parameter also affecting solid-state matter for weakly-bound molecular crystals and gases. While the specific detection parameters will be affected by the state of matter (e.g. in a solid, the crystal lattice will exert damping forces which affect rotations and, hence, the correct microwave frequencies), the fact that the pulsed width needs to be in resonance with the states being probed is unchanged. As a specific example, consider FIG. 10 showing that for a series of states of RDX corresponding to wavenumbers between ~1250 and 1450 $cm^{-1}$, for the specific excitation frequency of 3 GHz, the difference between a signal which barely—if at all—stands out from the noise and a signal which is unmistakable and has a very high signal-to-noise ratio is the choice of a 32 nm pulse width rather than a 192 ns pulse width. In hindsight, one can see these features at the longer pulse width, but the low modulation strength makes it very difficult to use this information in any practical way.

Figure 11:
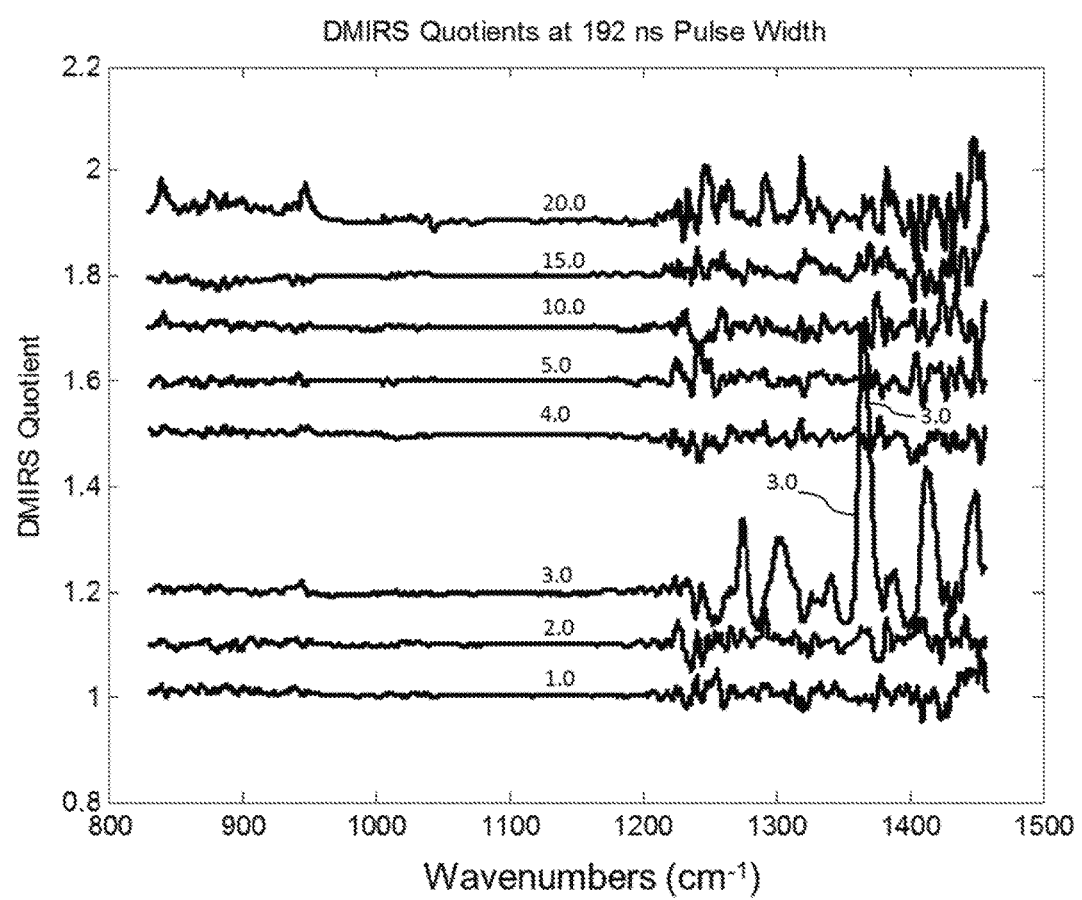
FIG. 11 shows the DMIRS results for RDX to 3 GHz pump radiation, outside in full sun, using 32 ns pulses at the microwave frequencies (e.g., 20.0, 15.0, 10.0, etc.), indicated.

As a reminder that all three parameters (wavelength, frequency and pulse width) need to be selected correctly, FIG. 11 shows the change in modulation and, for that matter, the types of changes (enhancement or suppression and the location of these effects) as the microwave frequency changes. If the parameter set is far from optimal, the response will be weak. See the curves (representing 1 and 15 GHz). When optimized, even in solids, the modulation can be significant, as is evident from the 5.0 microwave frequency curve (3 GHz).

Practical Ramifications: Mixtures

Figure 12:
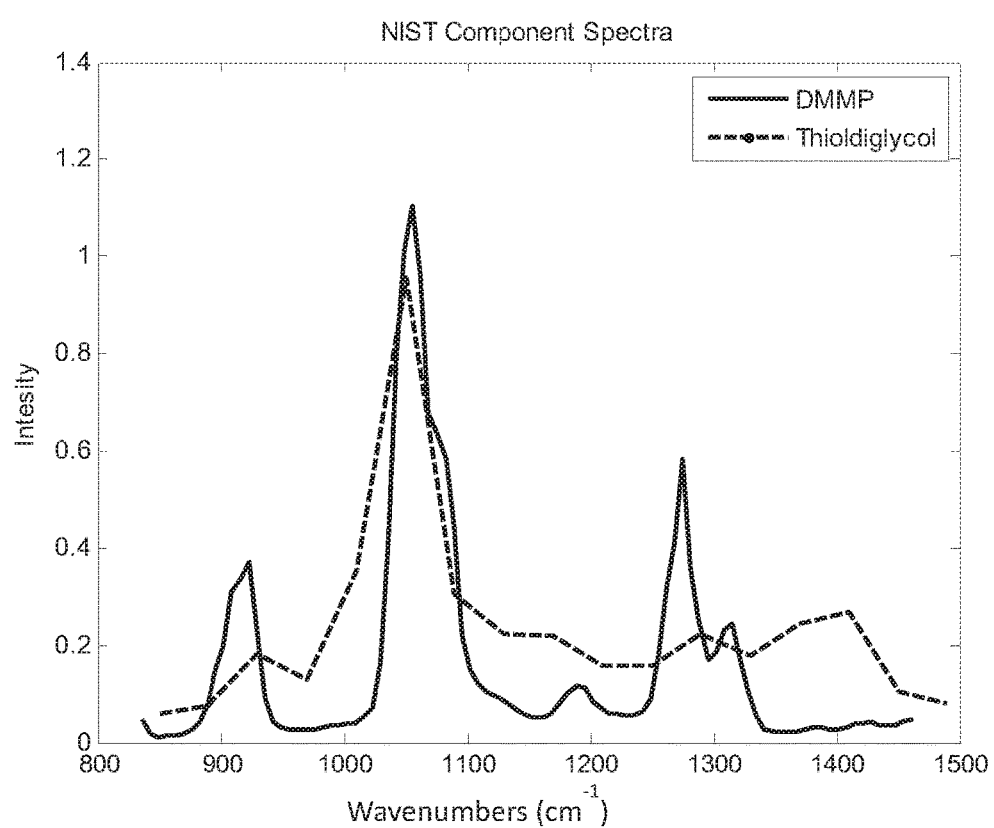
FIG. 12 shows the pure component spectra of thiodiglycol (dashed line) and DMMP (solid line) obtained from the National Institute of Standards (NIST).

A common difficulty in spectroscopic analysis is resolving individual molecular species in complex mixtures. Cases where spectral overlap is high make resolving individual components from the convolved spectra difficult. Infrared spectra of mixtures are comprised of peaks from each component making separation of peaks due to individual components a challenge. An example of this type mixture is thiodiglycol (CAS 111-48-8) and dimethyl-methylphosphonate (CAS 756-79-6) (DMMP). Standard infrared spectra for both components are presented in FIG. 12. Here the degree of overlap precludes elucidation of either species as both demonstrate simultaneous absorptions at nearly the same frequencies.

Common techniques for resolving mixtures generally involve post processing data and the ability to extract component information from additive individual spectra. This involves the approximation that the mixture spectrum is the sum of the pure components multiplied by the concentration of each species. This approximation is appropriate in cases where intermolecular interactions are low. However, in liquids these interactions, such as hydrogen bonding, cause shifts in spectral features, thus complicating the extrapolation to pure component spectra. This method is further complicated if the mixture is not known, or is in the presence of a varying background.

Figure 13:
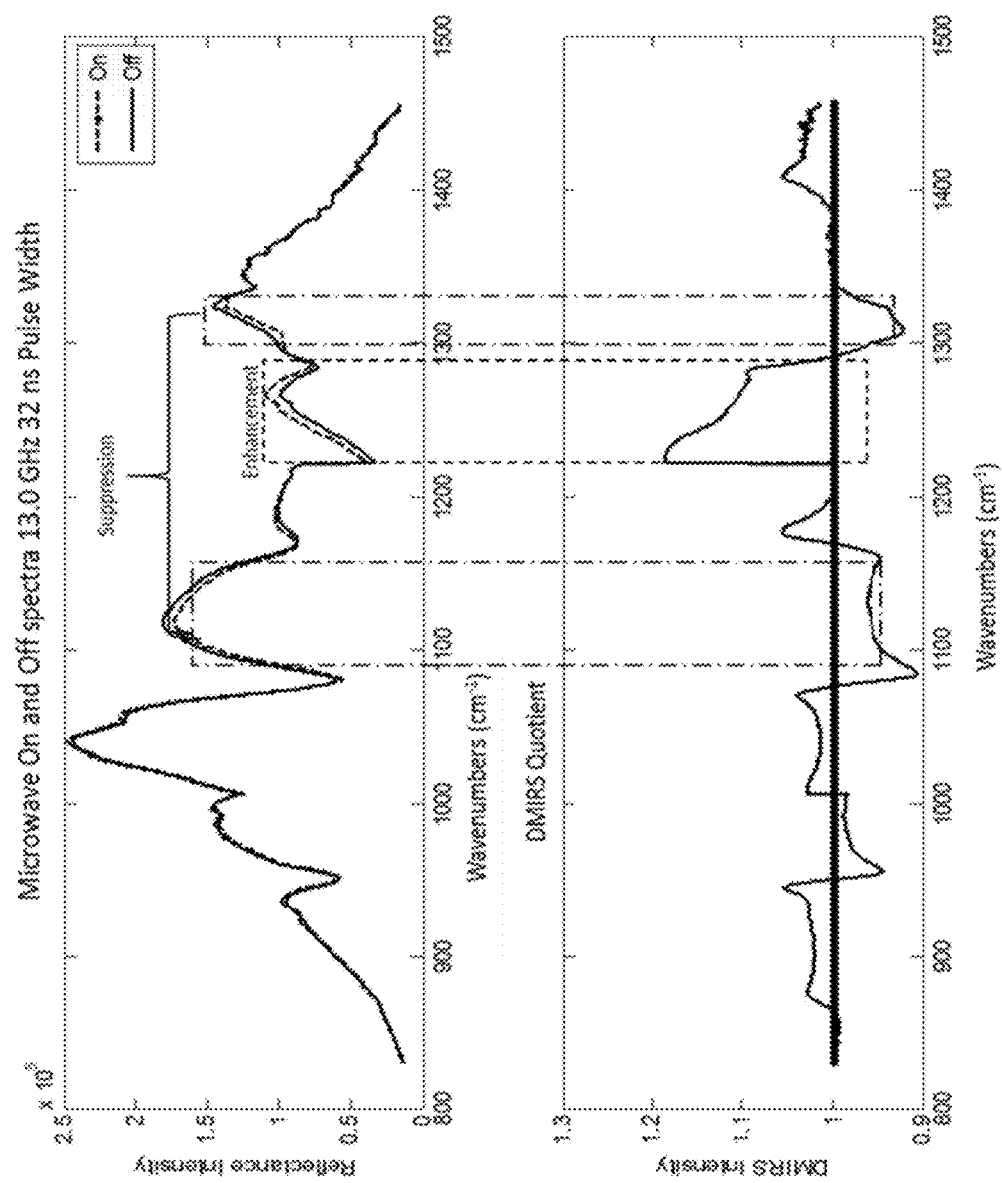
FIG. 13 (upper panel) shows the microwave on and off spectra for thiodiglycol, and (lower panel) DMIRS quotient for thiodiglycol at 13.0 GHz, 32 ns pulse width. The bars defined by the dash/dot line indicate transition suppressions, and the bar defined by the dash line indicates an enhancement.
Figure 14A:
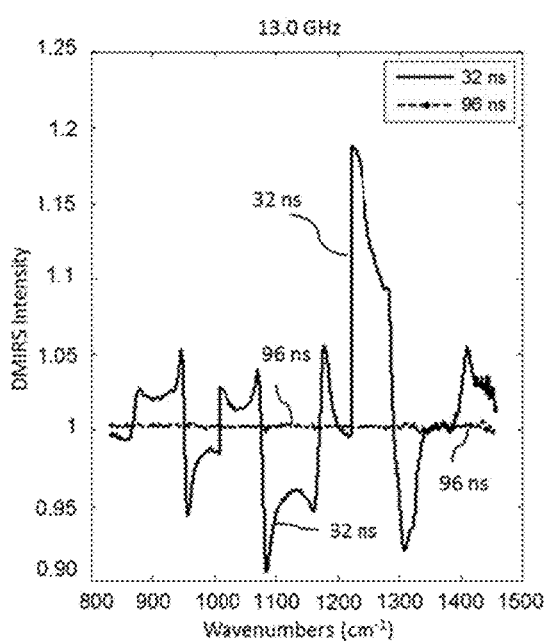
Figure 14B:
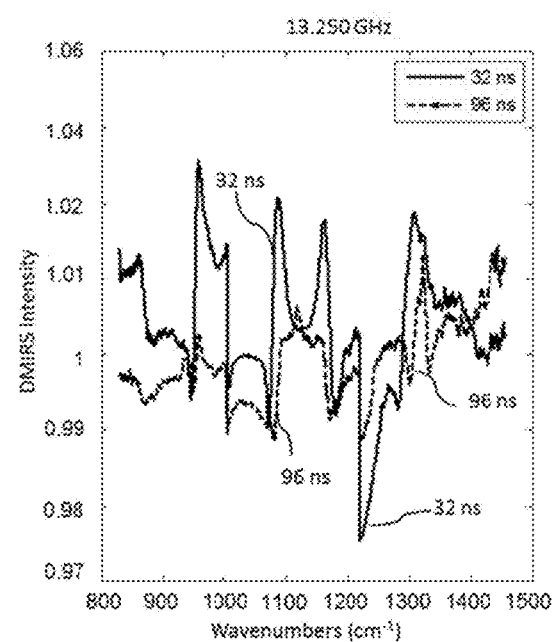
Figures 14C, 14D:
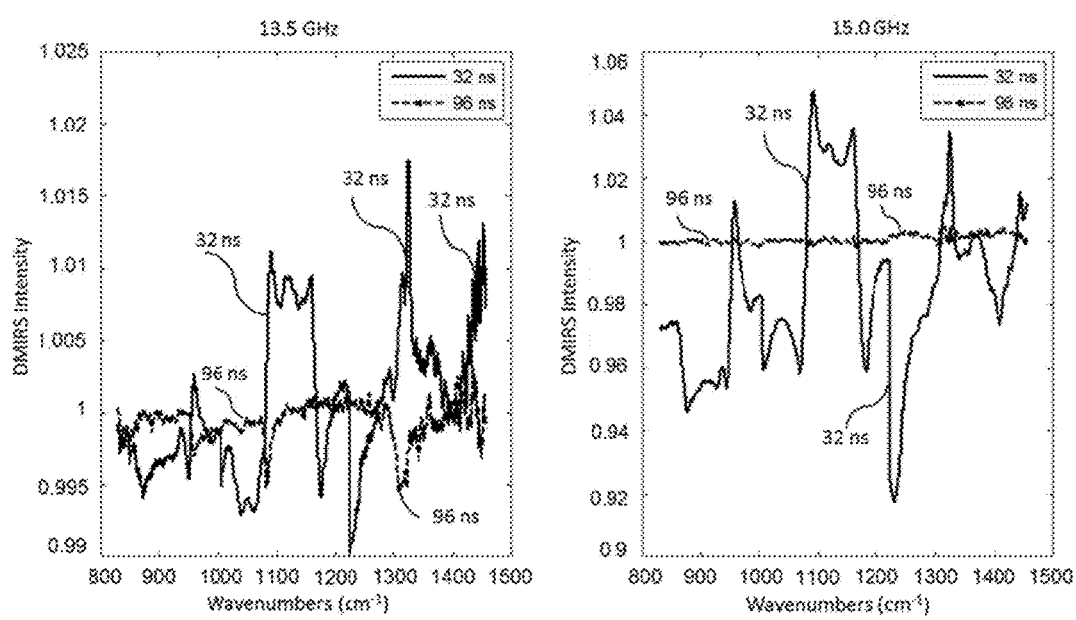

An alternate approach is to take advantage of enhanced selectivity gained from multi-dimensional interrogation of the sample via the DMIRS technique of the present invention. For a given species there are a set of microwave frequencies that can be observed as rovibrational states in the DMIRS spectrum. Within these states there is a resonant pulse width, which produces an increase in the observed modulation. By optimizing the pulse width for a particular rovibrational state, the transition of interest can be enhanced, or suppressed. This phenomena is shown in FIG. 13 for a liquid sample of thiodiglycol. The figure demonstrates the enhancement and suppression in the raw on and off spectra (top figure) as well as the resulting quotient (on/off) (bottom figure). The bars in the range identified by the dash/dot lines indicate transition suppressions, while the bar in the range identified by the dashed line indicates an enhancement.

The influence of the pulse width on differential MW spectrum is demonstrated in the comparison of DMIRS quotients collected at two pulse widths for a variety of pump frequencies ranging from 13-15.5 GHz (FIGS. 14A-F). Here thiodiglycol was excited using 32 (solid curves) and 96 (dashed curves) ns pulses and microwave frequencies were determined through prior empirical observation. The 13.0 GHz data in the upper left corner (FIG. 14A) shows almost 20% modulation for the feature spanning 1200 $cm^{-1}$ to 1300 $cm^{-1}$ at the 32 ns pulse width, but far lower modulation at 96 ns. Similar qualitative effects are seen for the other pump frequencies, although the specific details are quantitatively different for each of the cases. The low modulation at 15.25 and 15.50 GHz suggests that these excitation frequencies are far from optimal. It is important to note that the resonance pulse width may only apply to a single transition, so optimizing the DMIRS technique for an analyte of interest either requires a priori knowledge or a rigorous treatment of all experimental parameters, but the technique can then be tuned to discriminate interference, environment, and competing species. As a qualitative measure of determining if a molecular species of interest is present, the unique ability to invert a feature from an enhancement to a suppression is useful, and is demonstrated by comparing several features in the 13.0 GHz data (FIG. 14A) and at 15.0 GHz FIG. 14D). Resonance condition serves to enhance specific transitions, as also demonstrated at 13.0 GHz and 15.0 GHz, where the 32 ns solid curve is almost mirrored around the horizontal axis. FIGS. 8 and 9 were extracted from this data.

Mixture Analysis

Pure thiodiglycol, pure DMMP, and a 50/50 mixture of DMMP/thiodiglycol were interrogated using three pulse widths and seven microwave frequencies each optimized for either a DMMP or thiodiglycol transition. The experimental matrix and observed results are shown in the table of FIG. 15, peak enhancements are indicated with a (+), suppressions with a (−), and if no effect is observed (N.O.).

A comparison of optimal microwave perturbation and pulse width is presented for the DMMP/thiodiglycol mixture at 13.0 GHz with 32 ns pulse width and 4.116 GHz with 256 ns pulses in FIGS. 16A and B. FIG. 16A shows the previously shown modulation for thiodiglycol at 32 ns pulse width. The mixture data closely mirrors the pure thiodiglycol data, with virtually no response attributable to DMMP. The modulation is lower for the mixture spectrum (12% as compared to 20%), but this can be ascribed to the mixture being diluted with non-responding DMMP molecules. The response for thiodiglycol is quite broad at the short pulse width, with most of the spectrum showing some degree of modulation. Similarly, FIG. 16B displays the response for DMMP at 4.116 GHz observed with 256 ns pulse width. Once again the mixture response closely matches that of pure DMMP, and has broad response, especially for the low energy portion of the spectrum. In both cases the interesting result may not be the optimized response of either analyte, but the lack of response from the interferent.

Interferents

Figure 17:
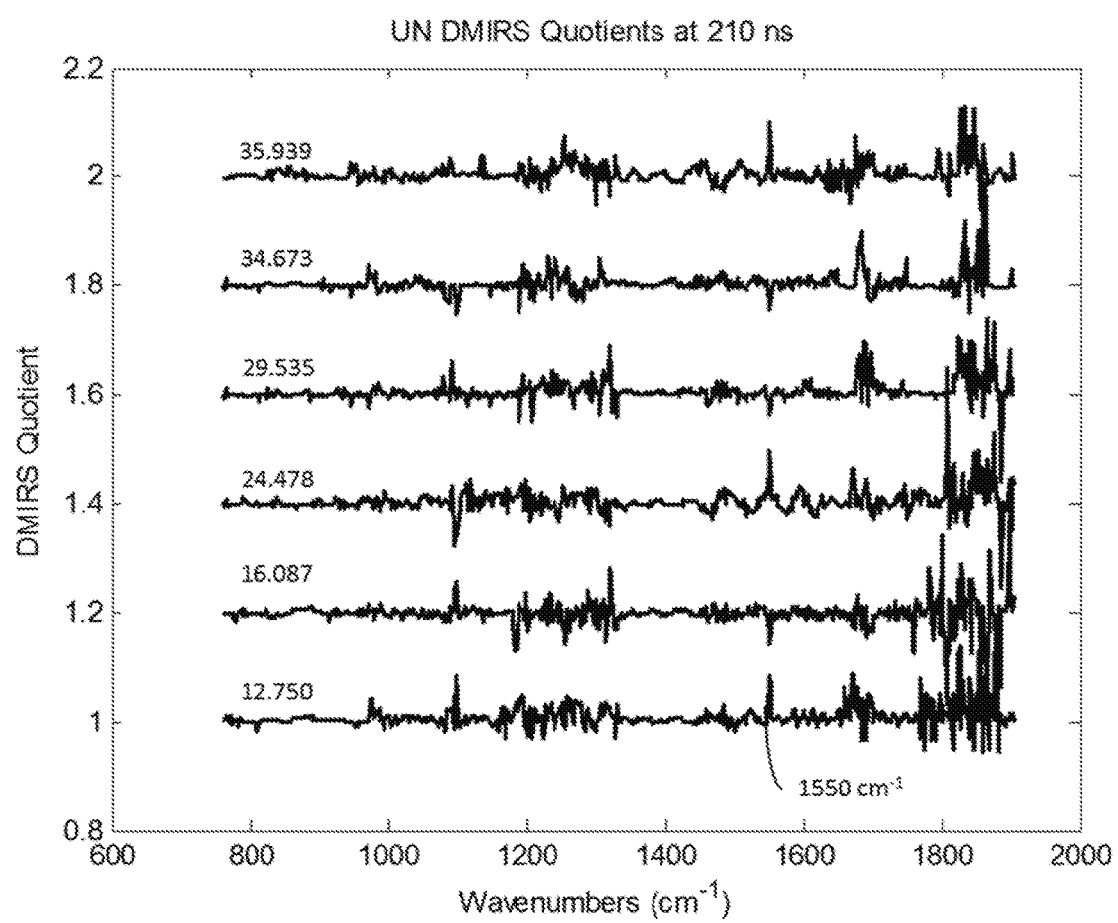
FIG. 17 shows the DMIRS response of urea nitrate (UN) at 210 nm at various excitation frequencies in GHz as indicated (e.g., 35.939, 34.673, 29.535, etc.).
Figure 19A:
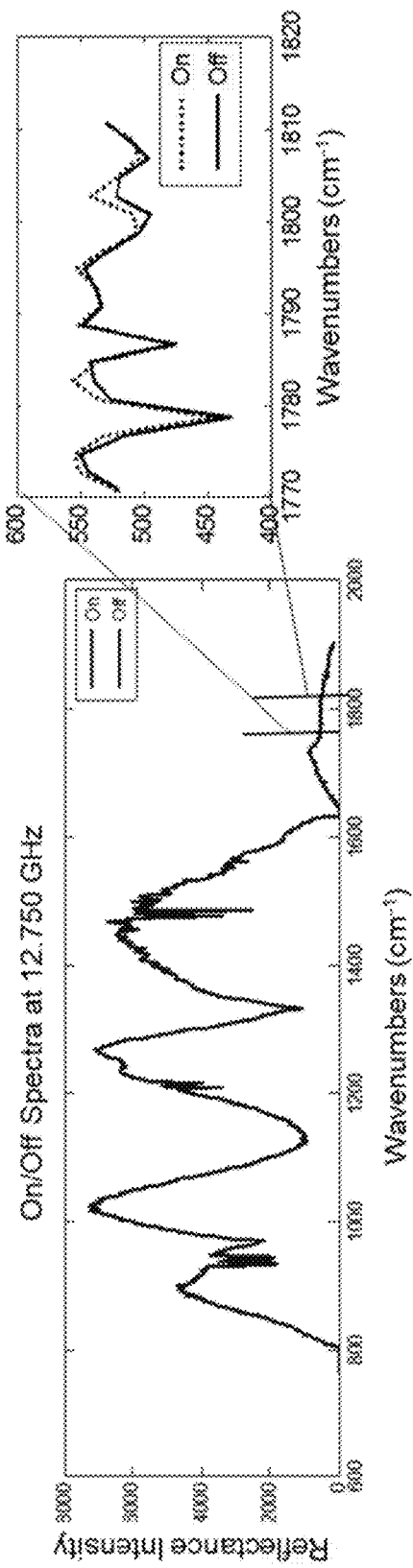
FIGS. 19A and B show the DMIRS response (raw data in A, quotient in B) for automotive door foam using the UN excitation parameters. As indicated in the legend, the dotted line represents "on" spectra; the solid line, "off" spectra.
Figure 19B:
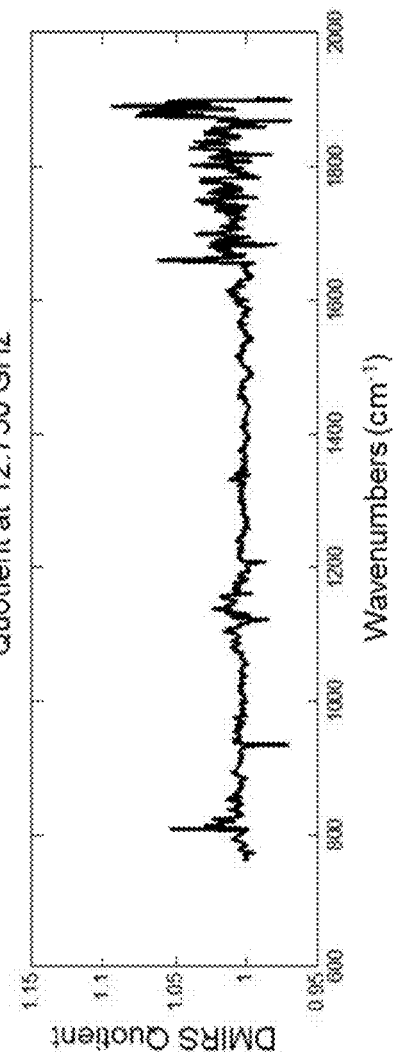
Figure 20:
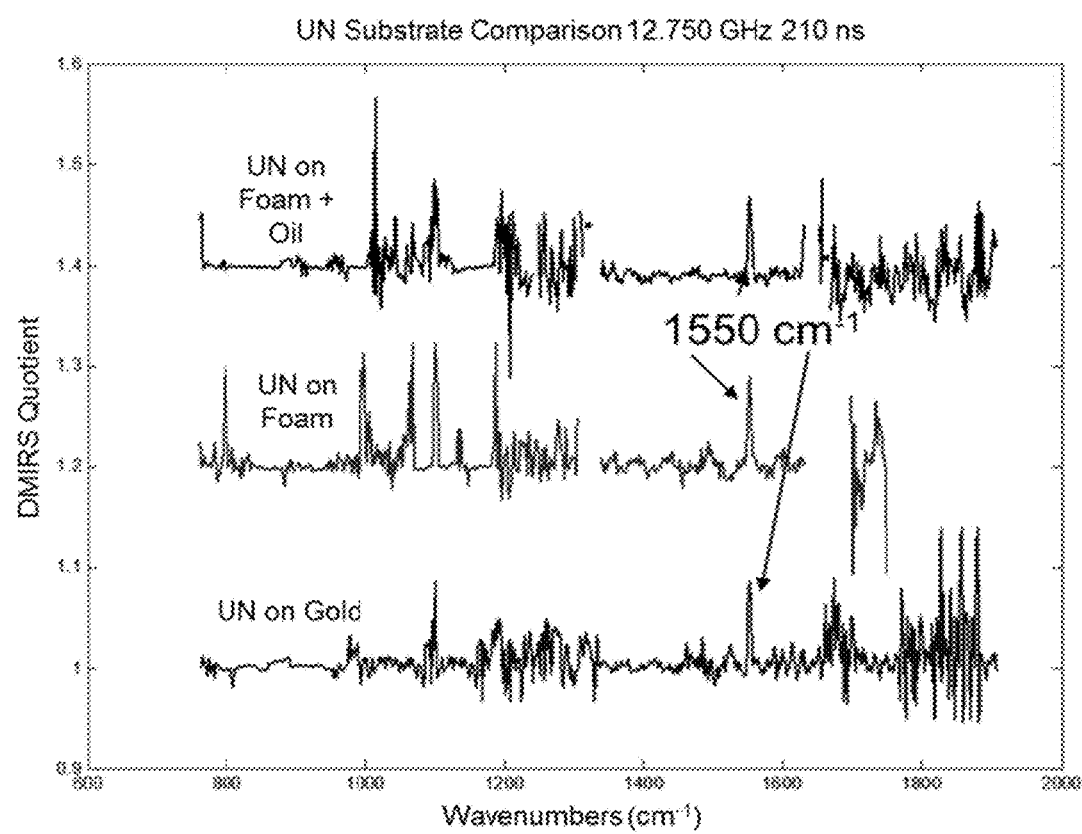
FIG. 20 shows the DMIRS response (quotient) at 1550 $cm^{-1}$ for UN is clearly visible on a laboratory (gold) substrate, on a foam substrate, and on a foam substrate with a 5W-30 motor oil coating.

The mixture problem may be viewed as identifying a specific molecule (or molecules) in a mixture, as was done in the previous example, or as immunity to interferents, namely: the ability to detect the molecule of interest, taking advantage of a priori knowledge about optimal excitation parameters. The immunity to interferents is demonstrated using an example of urea nitrate ("UN"). In a laboratory environment, urea nitrate was deposited on a gold substrate (gold being chosen for laboratory work as the reflectivity of gold is uniform across the IR spectral region). Under these circumstances, optimal detection parameters can be determined. Based on modeling results, DMIRS modulation at 1550 $cm^{-1}$ was predicted and observed experimentally. This effect is shown in FIG. 17, where the DMIRS response at several calculated UN excitation or pump frequencies is shown. Using the same detection parameters, 5W-30 motor oil shows no response, as shown in FIGS. 18A and B. (FIG. 18A shows the raw IR spectral data; FIG. 18B shows the calculated quotient.) Rubber automotive door foam similarly shows no response, as shown in FIGS. 19A and B. (FIG. 19A shows the raw IR spectral data; FIG. 19B shows the calculated quotient.) Considering the sequence of FIGS. 18A and B and FIGS. 19A and B, it comes as no surprise that FIG. 20 shows that the DMIRS effect clearly allows a molecule of interest to be seen in the presence of non-optimal, real-world substrates and interferent overcoats. This can be seen by considering the 1550 $cm^{-1}$ response in FIGS. 17 and 20 and the absence of said response in FIGS. 18B and 19B (the substrate and interferents).

Whereas the drawings and accompanying description have shown and described the preferred embodiments of the present invention, it should be apparent to those skilled in the art that various changes may be made in the forms and uses of the invention without affecting the scope thereof.

We claim:

1. Instrumentation for detecting for the presence of a molecular species in a sample based on the selective excitation of rotationally dressed states of such species while probing the affected rovibrational transitions of such species, the instrumentation including:
    a source of electromagnetic radiation for probing the sample to determine both an unperturbed response of the molecular species and a perturbed response of the molecular species;
    a source of electromagnetic radiation for perturbing the rovibrational density of states of the sample;
    apparatus for controlling the frequency of the radiation from the perturbing source;
    a detector for collecting photons that have interacted with the sample as a result of the response to the probing of the sample in the unperturbed and as a result of the perturbing of the sample; and
    means for determining the effect the perturbation had on the molecular species, the means for determining being coupled to the detector.

2. The instrumentation of claim 1, further including apparatus for controlling the pulse width of the radiation from the perturbing source.

3. The instrumentation of claim 1, wherein the means for determining the effect the perturbation had on the molecular species includes means for determining the change between the spectral response of the unperturbed and the perturbed rovibrational density of states of the molecular species.

4. The instrumentation of claim 3, wherein the means for determining the effect the perturbation had on the molecular species includes computer means.

5. The instrumentation of claim 4, wherein the computer means includes one or more data bases, including a data base in which a library of calibrated responses collected under known conditions from known concentrations of different molecular species is stored.

6. The method of detecting the presence of at least one molecular species in a sample with the instrumentation of claim 5; the method including:
    assessing the rovibrational density of states of the molecular species as manifested by the response of the molecular species in at least one region of the electromagnetic spectrum;
    assessing the perturbed state of the molecular species by perturbing the rovibrational density of states of the molecular species;
    determining the effects of the perturbation on the spectral response of the rovibrational density of states on the molecular species (herein the "response"); and
    comparing the molecular species response to the library of calibrated responses to identify the molecular species.

7. The instrumentation of claim 1, further including a gas cell for detecting for the presence of the molecular species in a gas phase sample.

8. The instrumentation of claim 1, further including a liquid cell for detecting for the presence of the molecular species in a liquid sample.

9. The instrumentation of claim 8, wherein the volume of the liquid cell is optimized to ensure that the volume available to be probed does not exceed the penetration depth of both the pump and probe radiation.

10. The instrumentation of claim 8, wherein the liquid cell has separate windows for the perturbing radiation and the probing radiation.

11. The method of detecting the presence of at least one molecular species in a sample with the instrumentation of claim 1; the method including:
    assessing the rovibrational density of states of the molecular species as manifested by the response of the molecular species in at least one region of the electromagnetic spectrum;
    assessing the perturbed state of the molecular species by perturbing the rovibrational density of states of the molecular species; and
    determining the effects of the perturbation on the spectral response of the rovibrational density of states on the molecular species.

* * * * *